(12) United States Patent
Smith et al.

(10) Patent No.: US 9,033,950 B2
(45) Date of Patent: *May 19, 2015

(54) METHOD FOR TRANSDERMAL DELIVERY OF PERMEANT SUBSTANCES

(75) Inventors: Alan Smith, Atlanta, GA (US); Jonathan A. Eppstein, Atlanta, GA (US); Bernadette Messier, Atlanta, GA (US); Zoran Novakovic, Atlanta, GA (US); Stuart McRae, Decatur, GA (US)

(73) Assignee: Nitto Denko Corporation (JP)

( * ) Notice: Subject to any disclaimer, the term of this patent is extended or adjusted under 35 U.S.C. 154(b) by 0 days.

This patent is subject to a terminal disclaimer.

(21) Appl. No.: 13/194,328

(22) Filed: Jul. 29, 2011

(65) Prior Publication Data

US 2012/0101426 A1 Apr. 26, 2012

Related U.S. Application Data

(63) Continuation of application No. 10/691,968, filed on Oct. 24, 2003, now Pat. No. 8,016,811.

(51) Int. Cl.
| *A61M 31/00* | (2006.01) |
| *A61K 9/00* | (2006.01) |
| *A61N 1/04* | (2006.01) |
| *A61M 37/00* | (2006.01) |
| *A61N 1/30* | (2006.01) |
| *A61N 1/32* | (2006.01) |

(52) U.S. Cl.
CPC ............ *A61K 9/0009* (2013.01); *A61K 9/0046* (2013.01); *A61M 2037/0007* (2013.01); *A61N 1/0412* (2013.01); *A61N 1/30* (2013.01); *A61N 1/327* (2013.01)

(58) Field of Classification Search
USPC ................ 604/20, 500, 501; 606/27; 600/309
See application file for complete search history.

(56) References Cited

U.S. PATENT DOCUMENTS

| 3,551,554 A | 12/1970 | Herschler |
| 3,711,602 A | 1/1973 | Herschler |
| 3,711,606 A | 1/1973 | Herschler |
| 3,964,482 A | 6/1976 | Gerstel et al. |
| 4,340,048 A | 7/1982 | Eckenhoff |
| 4,522,622 A | 6/1985 | Peery et al. |
| 4,537,776 A | 8/1985 | Cooper |
| 4,557,943 A | 12/1985 | Rosler et al. |
| 4,758,081 A | 7/1988 | Barnes |
| 4,764,164 A | 8/1988 | Sasaki |
| 4,767,402 A | 8/1988 | Kost et al. |

(Continued)

FOREIGN PATENT DOCUMENTS

| EP | 0 497 620 | 8/1992 |
| EP | 0 506 632 | 9/1992 |

(Continued)

OTHER PUBLICATIONS

Korean Office Action issued on Apr. 6, 2012.

(Continued)

*Primary Examiner* — Theodore Stigell
(74) *Attorney, Agent, or Firm* — King & Spalding LLP

(57) ABSTRACT

A method for delivering permeant substances transdermally into a membrane of an animal includes forming at least one delivery opening in the skin tissue, with the at least one delivery opening having a mean opening depth of between about 40 and about 90 microns.

12 Claims, 8 Drawing Sheets

(56) References Cited

U.S. PATENT DOCUMENTS

| | | |
|---|---|---|
| 4,775,361 A | 10/1988 | Jacques et al. |
| 4,820,720 A | 4/1989 | Sanders et al. |
| 4,844,098 A | 7/1989 | Mitchen |
| 4,855,298 A | 8/1989 | Yamada et al. |
| 4,860,743 A | 8/1989 | Abela |
| 4,863,970 A | 9/1989 | Patel et al. |
| 4,921,475 A | 5/1990 | Sibalis |
| 4,942,883 A | 7/1990 | Newman |
| 4,973,468 A | 11/1990 | Chiang et al. |
| 5,003,987 A | 4/1991 | Grinwald |
| 5,006,342 A | 4/1991 | Cleary et al. |
| 5,016,615 A | 5/1991 | Driller et al. |
| 5,019,034 A | 5/1991 | Weaver et al. |
| 5,041,109 A | 8/1991 | Abela |
| 5,092,864 A | 3/1992 | Hayes et al. |
| 5,115,805 A | 5/1992 | Bommannan et al. |
| 5,137,817 A | 8/1992 | Busta et al. |
| 5,139,023 A | 8/1992 | Stanley et al. |
| 5,165,418 A | 11/1992 | Tankovich |
| 5,169,389 A | 12/1992 | Kriesel |
| 5,171,215 A | 12/1992 | Flanagan |
| 5,190,558 A | 3/1993 | Ito |
| 5,215,520 A | 6/1993 | Shroot et al. |
| 5,223,219 A | 6/1993 | Subramanian et al. |
| 5,224,928 A | 7/1993 | Sibalis et al. |
| 5,226,907 A | 7/1993 | Tankovich |
| 5,231,975 A | 8/1993 | Bommannan et al. |
| 5,246,437 A | 9/1993 | Abela |
| 5,250,023 A | 10/1993 | Lee et al. |
| 5,267,985 A | 12/1993 | Shimada et al. |
| 5,273,525 A | 12/1993 | Hofmann |
| 5,279,544 A | 1/1994 | Gross et al. |
| 5,318,514 A | 6/1994 | Hofmann |
| 5,323,769 A | 6/1994 | Bommannan et al. |
| 5,328,453 A | 7/1994 | Sibalis |
| 5,342,355 A | 8/1994 | Long |
| 5,362,307 A | 11/1994 | Guy et al. |
| 5,380,272 A | 1/1995 | Gross |
| 5,421,816 A | 6/1995 | Lipkovker |
| 5,423,803 A | 6/1995 | Tankovich et al. |
| 5,425,728 A | 6/1995 | Tankovich |
| 5,427,585 A | 6/1995 | Bettinger |
| 5,445,609 A | 8/1995 | Lattin et al. |
| 5,445,611 A | 8/1995 | Eppstein et al. |
| 5,458,140 A | 10/1995 | Eppstein et al. |
| 5,459,127 A | 10/1995 | Felgner et al. |
| 5,462,520 A | 10/1995 | Hofmann |
| 5,547,467 A | 8/1996 | Pliquett et al. |
| 5,548,140 A | 8/1996 | Nguyen et al. |
| 5,554,153 A | 9/1996 | Costello et al. |
| 5,580,859 A | 12/1996 | Felgner et al. |
| 5,582,586 A | 12/1996 | Tachibana et al. |
| 5,611,806 A | 3/1997 | Jang |
| 5,651,768 A | 7/1997 | Sibalis |
| 5,697,901 A | 12/1997 | Eriksson |
| 5,713,845 A | 2/1998 | Tankovich |
| 5,749,847 A | 5/1998 | Zewert et al. |
| 5,752,949 A | 5/1998 | Tankovich et al. |
| 5,801,057 A | 9/1998 | Smart et al. |
| 5,817,089 A | 10/1998 | Tankovich et al. |
| 5,879,326 A | 3/1999 | Godshall et al. |
| 5,882,317 A | 3/1999 | Saito et al. |
| 5,885,211 A | 3/1999 | Eppstein et al. |
| 5,925,035 A | 7/1999 | Tankovich |
| 5,947,921 A | 9/1999 | Johnson et al. |
| 5,983,136 A | 11/1999 | Kamen |
| 6,013,318 A | 1/2000 | Hunt et al. |
| 6,022,316 A * | 2/2000 | Eppstein et al. .............. 600/309 |
| 6,027,459 A | 2/2000 | Shain et al. |
| 6,048,337 A | 4/2000 | Svedman |
| 6,050,988 A | 4/2000 | Zuck |
| 6,056,738 A | 5/2000 | Marchitto et al. |
| 6,071,249 A | 6/2000 | Cunningham et al. |
| 6,071,251 A | 6/2000 | Cunningham et al. |
| 6,083,196 A | 7/2000 | Trautman et al. |
| 6,117,290 A | 9/2000 | Say et al. |
| 6,138,044 A | 10/2000 | Svedman |
| 6,142,939 A | 11/2000 | Eppstein et al. |
| 6,148,232 A | 11/2000 | Avrahami |
| 6,173,202 B1 | 1/2001 | Eppstein |
| 6,183,434 B1 * | 2/2001 | Eppstein ........................ 604/22 |
| 6,230,051 B1 | 5/2001 | Cormier et al. |
| 6,247,485 B1 | 6/2001 | Rossi et al. |
| 6,251,083 B1 | 6/2001 | Yum et al. |
| 6,290,991 B1 | 9/2001 | Roser et al. |
| 6,334,856 B1 | 1/2002 | Allen et al. |
| 6,352,506 B1 | 3/2002 | Eppstein et al. |
| 6,451,240 B1 | 9/2002 | Sherman et al. |
| 6,503,231 B1 | 1/2003 | Praysnitz et al. |
| 6,508,785 B1 | 1/2003 | Eppstein |
| 6,527,716 B1 | 3/2003 | Eppstein |
| 6,659,982 B2 | 12/2003 | Douglas et al. |
| 6,692,456 B1 * | 2/2004 | Eppstein et al. ................. 604/22 |
| 6,708,060 B1 | 3/2004 | Avrahami et al. |
| 6,711,435 B2 | 3/2004 | Avrahami |
| 6,730,028 B2 | 5/2004 | Eppstein et al. |
| 6,887,202 B2 | 5/2005 | Currie et al. |
| 6,906,540 B2 | 6/2005 | McQuade |
| 7,041,057 B1 | 5/2006 | Faupel et al. |
| 7,048,723 B1 | 5/2006 | Frazier |
| 7,070,590 B1 | 7/2006 | Santini |
| 7,108,681 B2 | 9/2006 | Gartstein |
| 7,131,987 B2 | 11/2006 | Sherman |
| 7,141,034 B2 | 11/2006 | Eppstein et al. |
| 7,392,080 B2 | 6/2008 | Eppstein et al. |
| 7,758,561 B2 | 7/2010 | Eppstein |
| 8,016,811 B2 * | 9/2011 | Smith et al. .................... 604/501 |
| 2002/0010414 A1 | 1/2002 | Coston et al. |
| 2002/0131994 A1 | 9/2002 | Schur et al. |
| 2002/0138049 A1 | 9/2002 | Allen et al. |
| 2003/0078499 A1 | 4/2003 | Eppstein |
| 2003/0092982 A1 | 5/2003 | Eppstein |
| 2003/0097127 A1 | 5/2003 | Avrahami |
| 2004/0039342 A1 | 2/2004 | Eppstein |
| 2004/0220456 A1 | 11/2004 | Eppstein |
| 2005/0165393 A1 | 7/2005 | Eppstein |
| 2009/0264810 A1 | 10/2009 | Eppstein |

FOREIGN PATENT DOCUMENTS

| | | |
|---|---|---|
| EP | 0 514 258 | 11/1992 |
| GB | 2 153 233 | 8/1985 |
| GB | 2 221 393 | 2/1990 |
| JP | 2000-513971 | 10/2000 |
| JP | 2001-512329 | 8/2001 |
| JP | 2003-529401 | 10/2003 |
| WO | WO 92/00106 | 1/1992 |
| WO | WO 93/07801 | 4/1993 |
| WO | WO 93/20745 | 10/1993 |
| WO | WO 94/08655 | 4/1994 |
| WO | WO 94/09713 | 5/1994 |
| WO | WO 95/10223 | 4/1995 |
| WO | WO 96/00110 | 1/1996 |
| WO | WO 96/17648 | 6/1996 |
| WO | WO 96/41657 | 12/1996 |
| WO | WO 97/04832 | 2/1997 |
| WO | WO 97/07734 | 3/1997 |
| WO | WO 98/00193 | 1/1998 |
| WO | WO 98/22719 | 5/1998 |
| WO | WO98/29134 | 7/1998 |
| WO | WO 98/29134 | 7/1998 |
| WO | WO 99/29364 | 6/1999 |
| WO | WO 99/40848 | 8/1999 |
| WO | WO 99/43350 | 9/1999 |
| WO | WO 99/44507 | 9/1999 |
| WO | WO 99/44508 | 9/1999 |
| WO | WO 99/44637 | 9/1999 |
| WO | WO 99/44638 | 9/1999 |
| WO | WO 99/44678 | 9/1999 |
| WO | WO 00/03758 | 1/2000 |
| WO | WO 00/04821 | 2/2000 |
| WO | WO 00/04832 | 2/2000 |
| WO | WO 00/15102 | 3/2000 |
| WO | WO 00/27473 | 5/2000 |

(56) References Cited

FOREIGN PATENT DOCUMENTS

| WO | WO 00/74767 | 12/2000 |
|---|---|---|
| WO | WO01/13989 | 3/2001 |
| WO | WO 02/056939 | 7/2002 |
| WO | WO 03/039620 | 5/2003 |
| WO | WO 03/077970 | 9/2003 |
| WO | WO 2006/131931 | 12/2006 |

OTHER PUBLICATIONS

English translation of Korean Office Action issued on Apr. 6, 2012.
"After bite's unique formula key to efficacy" news release (no author), Tender Corporation, Littleton, NH, Aug. 1994.
Gustin et al. "Effects of Atmospheric Ammonia on Pulmonary Hemodynamic and Vascular Permeability in Pigs: Interactions with Endiotoxins," *Toxicology and Applied Pharmacology* 125:17-26 (1994).
Jacques et al. "Controlled Removal of Human Stratum Corneum by Pulsed Laser," *J. Invest. Dermatol.* 88:88-93 (1987).
Lane et al., "Ultraviolet-laser Ablation of Skin," *Arch Dermatol.* 121:609-617 (1985).
Matsumoto "Effects of ammonia and histamine on lung irritant receptors in the rabbit," *Respiratory Physiology* 77:301-308 (1989).
Matsumoto et al. "Substance P Antagonist Does Not Block the Stimulation of Rapidly Adapting Pulmonary Stretch Receptors by Ammonia", *Lung* 172:31-45 (1994).
McClung et al. "Early Changes in the Permeability of the Blood-Brain Barrier Produced by Toxins As-sociated with Liver Failure," *Pediatric Research* 28 No. 3 227-231 (1990).
Pohl et al. "Microjet assisted dye-enhanced diode laser ablation of cartilaginous tissue" *SPIE* vol. 2134A of *Laser-Tissue Interaction* (1994) at pp. 1326-1328.
Santus et al. "Transdermal enhancer patent literature" *J. Control Release* 25:1-20 (1993).
Ueda et al. "Skin penetration-enhancing effect of drugs by phonophoresis" *J of Controlled Release.* vol. 37:291-297 (1995).
Zaki et al. "Potential Toxins of acute liver failure and their effects on blood brain permeability," *Experientia* 39, Birkhäuser Verlag, CH-4010 Basel/Switzerland:988-991 (1983).
Ziylan et al. "Changes in the permeability of the blood brain barrier in acute hyperammonemia. Effect of dexamethasone" *Mol Chem Neurpathol* 20:203-218 (1993).
Extended European Search Report for EP Patent Application No. 10185373 issued on Jul. 1, 2011.
Extended European Search Report for EP Patent Application No. 10182248 issued on Mar. 15, 2011.
Russian Office Action for Russian Patent Application No. 2009122870 mailed Apr. 15, 2013.
English translation of Russian office action as well as notification date of said office action mailed Apr. 29, 2013.
Matriano, James A., Macroflux Microprojection Array Patch Technology: A New and Efficient Approach for Intracutaneous Immunization, Pharmaceutical Research. Jan. 2002. vol. 19, No. 1.
Mukerjee, E.V., Microneedle Array with Integrated Microchannels for Transdermal Sample Extraction and *In Situ* Analysis. The 12th International Conference on Solid State Sensors, Actuators and Microsystems, Boston, Jun. 8-12, 2003.
Zharov, Vladimir P., Laser Ultrasonic Transport of Drugs in Living Tissues. Biomedical Engineering Department, Bauman Moscow University of Technology, Moscow 107005, Russia.
Donnelly, Ryan F., Optical Coherence Tomography is a Valuable Tool in the Study of the Effects of Microneedle Geometry on Skin Penetration Characteristics and in-skin Dissolution. Journal of Controlled Release 147 (2010) 333-341.
European Search Report for Application No. 04795823.6, mailed Dec. 12, 2014.

\* cited by examiner

METHOD FOR TRANSDERMAL DELIVERY OF PERMEANT SUBSTANCES

CROSS REFERENCE TO RELATED APPLICATIONS

This application is a continuation of U.S. application Ser. No. 10/691,968 filed Oct. 24, 2003 now U.S. Pat. No. 8,016,811, the entire contents of which is hereby incorporated.

TECHNICAL FIELD OF THE INVENTION

The present invention relates to the delivery of drugs transdermally into a body or the extraction of an analyte transdermally from a body. More particularly, the present inventive subject matter relates to the delivery of a drug or extraction of an analyte through a delivery opening in a membrane of the body.

BACKGROUND OF THE INVENTION

The skin presents the largest, most readily accessible biological membrane through which an analyte may be collected or a drug delivered. Mucosal and buccal membranes present feasible, but less accessible, sites for collection and delivery. Unfortunately, the skin and, to a somewhat lesser extent, the mucosal and buccal membranes, are highly resistant to the transfer of materials therethrough. The skin generally comprises two main parts: the epidermis and the dermis. The epidermis forms the outer portion of the skin, and itself comprises several distinct layers. The outermost layer of the epidermis, the stratum corneum, is composed of denucleated, keratinized, clear, dead cells, and is typically between 10-30 microns thick.

The stratum corneum is chiefly responsible for the well known barrier properties of skin. Thus, it is this layer that presents the greatest barrier to transdermal flux of drugs or other molecules into the body and of analytes out of the body. The stratum corneum, the outer horny layer of the skin, is a complex structure of compact keratinized cells separated by intercellular lipid domains. Compared to the oral or gastric mucosa, the stratum corneum is much less permeable to molecules either external or internal to the body. The stratum corneum is formed from keratinocytes, which comprise the majority of epidermis cells, that lose their nuclei and become corneocytes. These dead cells then form the stratum corneum, which is a very resistant waterproof membrane that protects the body from invasion by exterior substances and the outward migration of fluids and dissolved molecules. The stratum corneum is continuously renewed by shedding of corneocytes during desquamation and the formation of new corneocytes by the keratinization process.

The formation of micropores (i.e. microporation) or delivery openings through the stratum corneum to enhance the delivery of drugs has been the subject of various studies and has resulted in the issuance of patents for such techniques.

Paranjape, et al., "A PDMS dermal patch for non-intrusive transermal glucose sensing," (Sensors and Actuators, May 2003, 195-204) discloses a polydimethylsiloxane (PDMS) patch for performing controlled and non-invasive monitoring of glucose levels. The PDMS patch is used in conjunction with a microporation system to open micropores through the stratum corneum of a patient. The micropores are formed by ablating the skin tissue through the use of micro-heaters integrated on the side of the patch that contacts the skin. Monitoring of glucose levels is then achieved using the patch.

Tankovich, U.S. Pat. No. 5,165,418, discloses a method of obtaining a blood sample by irradiating human or animal skin with one or more laser pulses of sufficient energy to cause the vaporization of skin tissue so as to produce a hole in the skin extending through the epidermis and to sever at least one blood vessel, causing a quantity of blood to be expelled through the hole such that it can be collected. Tankovich '418 thus is inadequate for noninvasive or minimally invasive permeabilization of the stratum corneum such that a drug can be delivered to the body or an analyte from the body can be analyzed.

Tankovich et al., U.S. Pat. No. 5,423,803, discloses a method of laser removal of superficial epidermal skin cells in human skin for cosmetic applications. The method comprises applying a light-absorbing "contaminant" to the outer layers of the epidermis and forcing some of this contaminant into the intercellular spaces in the stratum corneum, and illuminating the infiltrated skin with pulses of laser light of sufficient intensity that the amount of energy absorbed by the contaminant will cause the contaminant to explode with sufficient energy to tear off some of the epidermal skin cells. Tankovich '803 further teaches that there should be high absorption of energy by the contaminant at the wavelength of the laser beam, that the laser beam must be a pulsed beam of less than 1 microsecond duration, that the contaminant must be forced into the upper layers of the epidermis, and that the contaminant must explode with sufficient energy to tear off epidermal cells upon absorption of the laser energy. This invention also fails to disclose or suggest a method of drug delivery or analyte collection.

Raven et al., WO 92/00106, describes a method of selectively removing unhealthy tissue from a body by administering to a selected tissue a compound that is highly absorbent of infrared radiation of wavelength 750-860 nm and irradiating the region with corresponding infrared radiation at a power sufficient to cause thermal vaporization of the tissue to which the compound was administered but insufficient to cause vaporization of tissue to which the compound had not been administered. The absorbent compound should be soluble in water or serum, such as indocyanine green, chlorophyll, porphyrins, heme-containing compounds, or compounds containing a polyene structure, and power levels are in the range of 50-1000 W/cm$^2$ or even higher.

Konig et al., DD 259351, teaches a process for thermal treatment of tumor tissue that comprises depositing a medium in the tumor tissue that absorbs radiation in the red and/or near red infrared spectral region, and irradiating the infiltrated tissue with an appropriate wavelength of laser light. Absorbing media can include methylene blue, reduced porphyrin or its aggregates, and phthalocyanine blue. Methylene blue, which strongly absorbs at 600-700 nm, and a krypton laser emitting at 647 and 676 nm are exemplified. The power level should be at least 200 mW/cm$^2$.

Early prototype microporation systems were successful in creating delivery openings in selected biological membranes, such as the skin, to allow the efficient delivery of permeant compounds into the subject's body. However, there still remains a need to quantify and more clearly describe optimal delivery openings in a biological membrane. More particularly, there exists a need to develop a method for consistently measuring the depth and morphology of the delivery opening in order to optimize the use of the microporation system in delivering therapeutically active substances and extracting analytes from the body to be analyzed.

While many of the early prototype microporation systems allow for delivery of permeant compounds across a biological membrane, the preferred mode of delivery for many of such compounds is still transcutaneously by way of an injection using a hollow needle coupled to a syringe. In other words, a large percentage of curent permeant agents are administered to a patient through the skin by a hypodermic needle, which punctures the skin and then delivers a liquid bolus of the drug formulation. There is also a need, therefore, for a method of transdermally delivering these sorts of permeant substances to a patient in need thereof wherein the serum concentration profile of the permeant in the body when delivered by the microporation system mimics that of a permeant delivered by way of a hypodermic needle.

SUMMARY OF THE INVENTION

The present inventive subject matter relates to a method for delivering permeant substances through a biological membrane of an animal comprising forming at least one delivery opening in the membrane, said at least one delivery opening having a mean opening depth of between about 40 and about 90 microns.

The present inventive subject matter further relates to a method for delivering drugs transdermally into a biological membrane of an animal comprising forming a plurality of delivery openings through a membrane, wherein said delivery openings have a distribution resulting in a bell-shaped curve with said delivery openings having a mean opening depth of between about 40 and about 90 microns.

The present inventive subject matter also relates to a method for evaluating the effectiveness of a microporator comprising the steps of: forming at least one delivery opening in a biological membrane of a mammal using said microporator, delivering a permeant substance across the area of the membrane with said at least one delivery opening, measuring the steady state serum concentration for said permeant substance, measuring the trans-epidermal water loss across the membrane of the mammal, and comparing the results of said measurements with known values for each which provide desired results.

Still further, the present inventive subject matter is directed to a method for evaluating the effectiveness of a microporator comprising the steps of: forming a plurality of delivery openings in a biological membrane of a mammal using said microporator, delivering a permeant substance across the area of the membrane with said at least one delivery opening, measuring the steady state serum concentration for said permeant substance, measuring the trans-epidermal water loss across the membrane of the mammal, and comparing the results of said measurements with known values for each which provide desired results, wherein said plurality of openings has a distribution resulting in a bell-shaped curve with said plurality of delivery openings having a mean opening depth of between about 40 and about 90 microns.

DETAILED DESCRIPTION

Figure 1:
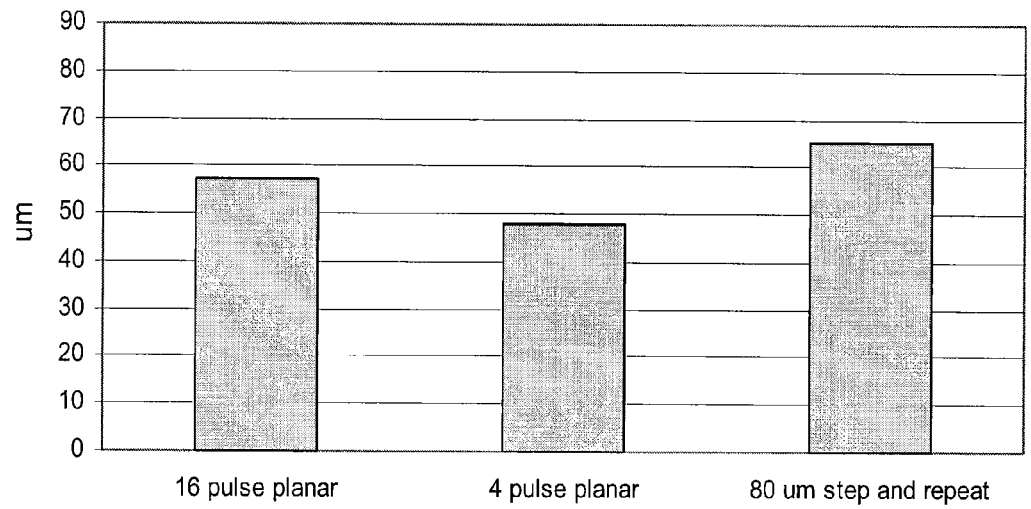
FIG. 1 represents manual focus depth measurements of planar array delivery openings and 80-micron step and repeat delivery openings.

It is noted that, as used within this specification and the attached claims, the singular forms of "a," "an," and "the" also include plural references unless the context clearly dictates otherwise. Therefore, for example, a reference to "a drug" includes a reference to a mixture of two or more drugs, or a reference to "an analyte" includes a reference to a mixture of two or more analytes. These examples are for illustrative purposes and are not meant to limit the disclosure in any way.

As used herein, "transdermal" or "transdermally" means passage of a permeant into and through the biological membrane to achieve effective therapeutic blood levels or local tissue levels of a permeant, or the passage of a molecule or fluid present in the body ("analyte") out through the biological membrane so that the analyte molecule maybe collected on the outside of the body.

As used herein, the term "bell-curve-type distribution" or "bell-curve" means a probability distribution function describing the relative frequency of occurrence of a certain value, such as the mean depth of a micropore or delivery opening. This distribution does not need to be symmetrical, Gaussian, of a beta-type distribution or any specific mathematically precisely defined distribution. This distribution may be described by a histogram showing step-wise jumps from one rang to another and depending upon the presentation, may even appear to b multimodal in nature.

"Minimally invasive," as used herein, refers to techniques in which a biological membrane or tissue is invaded by forming small holes, pores or openings in the surface of a tissue or membrane, but do not substantially damage the underlying, non-surface portions of the tissue or membrane.

As used herein, "OPTO" refers to a parametric setting of the activator system which delivers the programmed current pulse to the planar poration array. Specifically, the OPTO value is a numeric value falling within the range of 0 to 3000 wherein the higher the OPTO number is, the higher the peak temperature of the poration filaments is brought to in a specific pulse. The OPTO number is derived from a silicon photo-detector which is placed in the activator to planar array interface such that it is imaging the back side of the array of poration filaments. Upon activation, as the filaments begin to heat up, at a certain point enough radiosity is generated by them that this radiant energy can be detected and quantified by the silicon photo-detector, which produces an electrical output which is proportional to the temperature of the filaments within its field of view. This value is used as an input in a closed loop feedback control system which, once the prescribed OPTO value setting is reached, the control loop then holds this value by actively modulating the current being delivered to the array, thus holding the peak temperature a constant value for the duration of the programmed pulse width. In other words, an OPTO setting of 100 will cause the poration filaments to be brought to and held at a higher temperature than and OPTO setting of 25 regardless of the length of the programmed pulse width.

As used herein, "non-invasive" refers to techniques not requiring the entry of a needle, catheter, or other invasive medical instrument into the body.

"Delivery opening" refers to the removal of a portion of the biological membrane of an animal in order to lessen the barrier properties of the biological membrane, thus allowing easier passage of therapeutics and/or analytes across the biological membrane. If the biological membrane is the skin, a delivery opening is created by the removal of cells in the stratum corneum in a selected area of the skin. Preferably, the delivery opening will be no larger than about 1 mm in diameter, and more preferably no larger than about 100 microns in diameter and will extend through the stratum corneum sufficiently enough to break the barrier properties. As used herein, "delivery opening" is synonymous with "pore," "micropore," "opening," and "small hole."

"Biological membrane" means a membrane material present within a living organism, preferably an animal, more preferably a human, that separates one area of the organism with another. In many instances, the biological membrane separates the organism with its outer surroundings or environment. Non-limiting examples of biological membranes include the skin and mucous membranes in a human being.

As used herein, "opening depth," or "delivery opening depth" means the depth of the delivery opening made in the biological membrane. The opening depth is defined as the distance from the top surface of the biological membrane to the bottom of the delivery opening. Additional meaning to "opening depth" will be further defined below.

"Mean opening depth" refers to the mean, or average, depth of a delivery opening when more than one measurement of the depth of the delivery opening is made. For example, the opening depth may be measured by more than one person, the same person may measure the opening depth more than once, or the depth measurement may be taken in more than one location within the delivery opening. In such cases, the various measurements for a given delivery opening would be averaged in order to obtain the mean opening depth.

Also, "mean opening depth" refers the situation when a plurality of delivery openings is made within the biological membrane. The depth of each of the delivery openings is measured and the average of the depths is then calculated, providing one of ordinary skill in the art with the mean opening depth.

"Ablation" as used herein refers to the process of removing membrane tissue, preferably skin tissue, by applying a heated element, wherein the temperature of the heated element vaporizes the membrane tissue.

As used herein, "permeant" means any chemical or biological material or compound suitable for passage through a biological membrane of a mammal. Preferably, "permeant" refers to a therapeutic substance to be administered to a mammal. Non-limiting examples of such permeants are insulin, hydromorphone, vaccines and the like.

The present inventive subject matter is directed to a method for delivering drugs transdermally into an animal comprising forming at least one delivery opening in a membrane of the animal, with at least one opening having a mean opening depth of between about 40 and 90 microns. Preferably, the mean opening depth is between about 50 and about 70 microns. More preferably, the mean opening depth is between about 55 and about 65 microns. Even more preferably, the mean opening depth is about 60 microns. Not withstanding these preferred selected mean opening depths specified above, for each selected application of delivering a specific permeant, a more optimal selected mean opening depth may be determined experimentally by measuring the desired mean flux rate of the permeant through each delivery opening into the organism and then correlating these results with the target flux rate desired, the mean pore depth and the trans-epidermal water loss measurement of the porated skin surface.

The present inventive method includes the step of forming at least one delivery opening in a membrane of an animal. Preferably at least one delivery opening is formed in the skin of the animal. As used herein, "animal" means any mammal, and includes without limitation any mammalian subject, such as mice, rats, guinea pigs, cats, dogs, human beings, cows, horses, sheep or other livestock. "Animal" and "mammal" are used interchangeably herein. The animal is preferably a human being.

Further contemplated within the scope of the present inventive subject matter is a method for delivering drugs into an animal comprising forming a plurality of delivery openings in a membrane of the animal, with a majority of the plurality of delivery openings having a mean opening depth within the range of about 40 to about 90 microns. Preferably, about 75% of the plurality of delivery openings have a mean opening depth falling within the range of about 50 to about 70 microns. More preferably, about 75% of the plurality of delivery openings have a mean opening depth falling within the range of about 55 to about 65 microns.

As used herein, "majority" means more than half of the delivery openings formed in the membrane. Preferably, majority means between 60% and 80% of the delivery openings formed in the membrane. More preferably, "majority" means about 75% of the delivery openings formed in the membrane.

The present inventive subject matter is also drawn to a method for measuring the depth of a delivery opening. As has been previously stated, the microporation of a membrane is known in the art. However, heretofore, no one has attempted to characterize the depth of the delivery opening that is formed by a microporation device and establish the relationship between the mean depth of th opening and the flux into the organism through the opening.

Difficulties are inherent in attempting to consistently characterize a delivery opening or a group of delivery openings. A large number of variables are present which may affect the measurement of the morphology of the delivery opening. The variables include, but are not limited to, the shape of the membrane, the normal surface variations in the biological membranes, variations in contemporaneous physiological conditions such as whether the subject is sweating, has chill bumps or is very hairy, the contact surface area between the microporation device and membrane, any motion of the biological membrane being observed and imaged, moisture on the surface, the effect of heartbeat, etc.

It has been determined that the size of the delivery opening, including the depth thereof, helps determine the rate at which a permeant substance is taken into the body across the membrane, or an analyte is taken out of the body across the membrane. In other words, the size and depth of the delivery opening are important variables in determining the flux rate of the substance across the membrane. For permeant substances which have large molecules, for instance insulin which is normally formulated as a hexamer with a molecular weight of about 36,000 Daltons, a larger and deeper delivery opening is needed in order to achieve the desired flux of the insulin across the membrane than that needed for a smaller molecule such as hydromorphone (molecular weight of about 300 Daltons).

The early prototype microporation systems were effective in providing openings in membranes for delivering or extracting substances across the membrane. Since the early prototype microporation systems were effective in delivering drugs, the second generation microporation systems were developed in order to mirror the results (for example, the depth of the micropores) of the early prototype systems. In order to evaluate both first and second generation prototype microporation systems, the dimensions of the micropores created by each system first have to be characterized. The present inventive method allows one of ordinary skill in the art to conduct such a characterization. The present inventive method allows the opening depth and mean opening depth to be consistently measured, regardless of the microporation system used.

Preferably, the present inventive methodology provides means for characterizing the dimensions of a plurality of micropores wherein the statistical summary of these measurements results in a bell-curve-type distribution of opening depths, with the mean opening depth being at the "peak" of the curve. After creation of the delivery openings, the opening depth is determined according to the present inventive method. The opening depth of the openings is measured using appropriate equipment. A non-limiting example of an apparatus for determining the opening depth of a plurality of openings is a video microscope in conjunction with a marking and measurement system. However, other such measurement equipment may also be used within the scope of the present inventive subject matter.

In a preferred embodiment, the opening depth is measured using a microscope and digital depth indicator. The spring-loaded indicator is positioned so that the end of the indicator gauge rests on the flat surface of a stage of a microscope. The zero function of the indicator is used to record the distance in the 'Z' direction of the opening, namely the depth of the opening. One of ordinary skill in the art brings the top surface of the membrane into focus, at which point the digital indicator is zeroed. The stage is then moved downward in very small increments until the bottom of the opening comes into focus. The distance that the stage is moved between the zeroed position and the position in which the bottom of the pore is in focus is recorded as the opening depth. The objective used on the microscope is selected to have a short enough depth of field to allow the operator to clearly distinguish at what position in 'Z' the center of view is in focus.

The depth of an opening may be measured multiple times at multiple different positions within the opening and referencing multiple different positions along the upper edge of the opening, by different individuals, to provide a mean opening depth for that opening. In addition, the depth may be measured to various positions along the bottom of the opening to provide a mean opening depth for that opening. In either case, the mean opening depth is recorded as the opening depth for that opening. It is often advantageous to use the mean opening depth for a particular opening due to a number variables that influence the opening depth. The variables include the roughness of the membrane, the slope of the membrane sample (the membrane sample may not be exactly planar), the contact surface of the microporation device, pressure, and hydration of the membrane sample. The use of the mean opening depth helps minimize the effects of these variables on the measurements of different openings.

The depth of an opening may also be measured by infusing a tracer compound, such as a liquid which has been formulated to fluoresce, but has also been designed to minimize the effusion of this liquid from the opening itself into the surrounding tissues structures within the time frame within which the opening will be measured. In this case, a fluorescent microscope can be used to image the opening and by calibrating the intensity of the fluorescence produced by the tracer, an accurate profile of the opeing can be computed. Alternatively, by selecting a fluorophore which absorbs and fluoresces at wavelengths were there is little native effect on these photons by the intervening and surrounding tissue, a confocal fluorescent microscope can be used to accurately measure the openings even if the outer most portion of the opeing flaps back together, obscuring a clear optical view into the bottom regions of the opening. The confocal system can easily scan through these tissues and map out the full three dimensional profile of the opening within the biological membrane, such as the skin. A suitable fluorophore for this purpose would be one constructed of inert, polymer microspheres in suspension in water with peak absorption in the 600 to 800 nanometer wavelength range and peak emissions in the 650 to 850 nanometer range, such Micro Probes' (Eugene, Oreg.) FluoroSpheres Flurescent Color Kit F-10720.

Additionally, a depth measurement assessment of individual pores may be made by scanning a small electrode over the openings and measuring the complex impedance between the electrode and a second counter-electrode placed some distance away on the organism. As the resistivity of the outermost layers of mammalian skin is typically much higher than the deeper layers of the epidermis and dermis, this measurement of impedance can be correlated to the depth of the individual pores, as measured by other means. Similarly the trans-epidermal water loss (TEWL) measurements described earlier can be used to assess the mean depth of a plurality of micropores.

One or more of these measurement procedures is repeated for each opening created by the microporation system, providing a range of data for the particular microporation system. As the number of individual openings formed by a given version of the microporation system, the power of the statistics to characterize the mean depth values increases. Preferably, the range of data provides a bell-curve-type distribution of opening depths, with the mean opening depth of the openings created by the microporation system being at the peak value of the curve and being used as the representative depth for that microporation system. In addition, it is desirable to have a narrow range encompassed by the distribution created by a particular microporation system. A narrower range in the distribution will allow for more consistent flux rate of the permeant across the membrane from opening to opening. Thus, it is preferred that the mean opening depths of the delivery openings have a range of depths falling within one standard deviation of about 50 to about 70 microns. More preferably, the mean opening depths of the delivery openings will have a range within one standard deviation of about 60 microns.

The target mean opening depth for a microporation system is that depth at which the openings allow for acceptable flux of a permeant across the membrane. In other words, if the permeant to be delivered is a small molecule like hydromorphone, the target mean opening depth will be smaller than if the permeant to be delivered is a larger molecule or even a particle, like insulin or a nanoparticle. For example, if hydromorphone is to be delivered, then the acceptable mean opening depth may be about 40-60 microns. However, if insulin is to be delivered, then the acceptable mean opening depth may be about 65-90 microns. The present inventive subject matter also contemplates the delivery of vaccines, particles which may change some measurable state in response to a shift in level of a local analyte and other permeants transdermally.

In a preferred embodiment of the present inventive subject matter, the mean opening depth of the microporation system is between about 40 and about 90 microns. More preferably, the mean opening depth of the microporation system is between about 50 and about 70 microns, and even more preferably about 60 microns.

Within another preferred embodiment of the present inventive subject matter, about 75% of the openings created by the microporation system have a mean opening depth of between about 40 and about 90 microns, more preferably between about 55 and about 65 microns, and even more preferably about 60 microns.

As microporation systems improve, it is contemplated within the scope of the present inventive subject matter that the bell-curve-type distribution of mean opening depths of a particular microporation system will tighten up, meaning that the range of mean opening depths will narrow. This is desirous since those openings that are too shallow do not allow proper flux of the permeant across the membrane, and those openings that are too deep often result in skin erythema and discomfort to the mammal. Optimally, the range of mean opening depths of openings from a particular microporation system is narrow enough to prevent openings that are too shallow or openings that are too deep.

An advantage provided by the present inventive subject matter is that the measurement of opening depth and mean opening depth is independent of the type of microporation system used. The present inventive subject matter may be used to determine the opening depth of any opening created by any microporation system.

In a preferred embodiment, the creation of delivery openings (micropores) through the stratum corneum for the purpose of delivering proteins and peptides, small hydrophilic molecules, particles, vaccines and genes through the skin is accomplished using a planar array microporation system. The technology is based on the application of energy to a small, spatially tightly defined area of the skins surface. One method of delivering this energy inot the skin is by placing the skin in direct contact with a tiny, electrically heated filament, with said filament being able to be rapidly modulated in temperature by pulsing a specified electrical current through it, causing it to heat up and thereby deliver to the skin a rapid pulse of energy into the region in immediatted proximity to the contact area. When a short duration electrical current pulse of energy is delivered to the skin the skin cells within this targeted zone are flash-vaporized leaving an opening through the stratum corneum allowing access into the living layers of the epidermis below. Alternatively, this planar array microporation system could use a matrix of sharp, micro-protrusions to form these breaches in the stratum corneum. After a pattern of micropores is created, a patch containing the drug or desired permeant is applied over the micropores. The delivery profile is determined by the following: the permeant concentration and formulation with other excipients such as surfactants, viscosity modifiers, organic solvents, enhancers designed to increase the permeability of the underlying layers of the skin, patch area, micropore density, and patch application time. The characteristics of the electrically heated filament (geometry, material, dimensions) and the activation paramteres (electrical current pulses duration, peak current level, pulse shape, etc.) determine the size and depth of the micropores that are created.

The size of the delivery opening (length, width, and depth) is critical to the amount of permeant that can be delivered in a given timeframe (flux rate). Traditional transdermal delivery literature suggests that to produce a dramatic increase in flux of any permeant that the depth of the delivery opening only had to be just past the thickness of the stratum corneum (15-30 microns thick). However, based on recent data which correlates the delivery opening dimensional profiling data and the resultant permeant flux rates, it appears that a larger and deeper openings are required to achieve adequate, or in some cases even measurable flux for certain molecules. Whereas much of the pore profiling data has been obtained using a model system (human donor cadaver skin), the dimensions of pores formed and the volume of skin tissue ablated correlate with in vivo drug delivery experimental data obtained on various animal models as well as humans in clinical studies (mainly with insulin and hydromorphone).

The critical dimensions of micropores required for delivery can be described in several ways: 1) critical depth/size surpassed for all micropores measured; 2) critical mean+/−standard deviation of the distribution of all micropores measured for a given pattern; and 3) percentage of micropores with a depth/size exceeding that of a certain target range of depth/size. Each of these have been discussed further above.

In defining the critical size of delivery openings created, it is important to realize the limitations of the techniques used to profile micropores. It is very difficult to quantitatively measure micropore dimensions directly in living subjects or humans due to the small microscopic scale (100 um) and the presence of significant motion artifact from involuntary muscle movements, and small blood vessel pulsing. Therefore, the present inventive subject matter methods, apparatus and techniques have been developed to study microporation both in synthetic skin surrogates, human cadaver skin, excised animal skin as well as living human and animal skin.

In addition, delivery of various permeants requires different flux rates depending on the permeant levels required for that compound. In the past, the depth and size of the micropores tested have been mainly limited to two representative compounds, insulin and hydromorphone, but are applicable to many other proteins, peptides small molecules, particles, vaccines and genes, as well.

Based on experience with the several preclinical and clinical studies, the following ranges have been determined: 1) the critical depth/size to be exceeded to allow meaningful flux through a given micropores is approximately 30 microns; 2) the target distribution has an approximate mean+/−standard deviation in the range of 50-60+/−10-15 microns; and 3) the percentage of micropores with a depth in the range of 40-90 microns is approximately 75%. 4) the percentage of micropores which have a depth which exceeds the 30 micron critical depth is approximately 90%. These target delivery opening depth characteristics have been obtained primarily based on clinical studies with a planar array of filaments.

It is preferred within the present inventive subject matter that the microporation system include a planar array microporator. Examples of a microporator with which the present inventive may be used to quantify the depth of the openings formed include, but are not limited to, a heated probe element capable of conductively delivering thermal energy via direct contact to a biological membrane to cause the ablation of some portion of the membrane deep enough to form a micropore the heated probe may be comprised of an electrically heated resistive element capable of ablating a biological membrane or an optically heated topical dye/absorber layer, electro-mechanical actuator, a microlancet, an array of microneedles (solid or hollow), microprojections, microcstructures or lancets, a sonic energy ablator, a laser ablation system, and a high pressure fluid jet puncturer. Preferably, the microporator includes a heated element that allows for rapidly modulating the temperature of the heated probe element.

A non-limiting example of a microporation system usable in the present inventive subject matter employs microneedles to make the delivery openings. Such a skin perforating device has a plurality of circular needle disks having skin perforation microneedles formed on the circumference of the disks. The device also has a central shaft that holds the needle disks in a face-to-face relationship with one another and allows rotation of the disks. The microneedles have a triangular shape and lateral sides of acute wave form. The microneedles in each of the needle disks are spaced apart at an equal pitch with the individual needle disks combined so that microneedles in one needle disk remain staggered from those of the adjoining needle disk.

In this non-limiting example, the delivery openings are formed by contacting the device to the membrane. The microneedles thus come into contact with the membrane. The needle disks of the device are, thereafter, rolled on the membrane while evenly pressing down the device on the membrane with a constant pressure. When rolling the device on the membrane with the constant pressure, the needle disks are rotated and the microneedles on their circumference create the delivery openings in the membrane. In this manner, the microneedles form the desired number of delivery openings of a given depth in the skin.

The use of microneedles is one example of a usable microporation system. Other such microporation systems are also usable in the methods of the present inventive subject matter. One other such system could use a planar array of individual electrodes, whereupon by applying an electrical potential to each electrode as referenced to a counter electrode, a local current flow through the contacted tissue can be established which delivers enough energy to produce the desired ablation and the formation of the micropore.

Another variable that affects the mean opening depth is the amount of pressure applied between the microporator in the microporation system and the membrane in which the openings are to be made. It is often desirous to apply positive pressure to the microporator in order to ensure contact between the microporator and the membrane sufficient to produce openings with the desired properties. The required physical contact pressure between the microporator filaments or electrodes and the tissue membrane required to facilitate the energy transfer may be achieved by applying vacuum to the microporator, thereby ensuring intimate contact between the microporator poration components and the membrane. Preferably the amount of vacuum applied between the microporator and the membrane is from about 0.25 bar to about 0.80 bar. More preferably, the amount of vacuum applied between the microporator and the membrane is about 0.50 bar.

Improved contact between the microporation system and the membrane aids in providing a narrower range of depths of delivery openings by ensuring that more microporation devices within the microporation system come into contact with the membrane. In addition to applying a vacuum between the microporation system and membrane as discussed above, improved contact is achieved by changing the properties of the substrate on which the microporators of the microporation system are housed. Surprisingly, by providing a rigid substrate, improved contact between the microporators and the membrane is achieved. Preferred materials to be used with the rigid substrate include a polyethylene film and a polyethylene film coated with an acrylic adhesive.

Another manner to improve the contact between the microporators and the membrane is to modify the surface of the planar array by adding projections that aid in establishing contact between the microporators and the membrane. The projections help stabilize planar array, thereby aiding in the contact between the microporators and the membrane.

The present inventive subject matter also involves the delivery profile of a permeant following formation of openings in a membrane. The optimal delivery profile for a microporation system is to mimic the delivery profile as if the drug is delivered subcutaneously across the membrane by a hypodermic needle. By optimizing the mean opening depth of the openings created by the microporation system, a delivery profile that mimics the profile of subcutaneous delivery is achieved. For example, insulin is administered to a mammal via an infusion pump and a subcutaneous cannula implanted in the subject at a prescribed rate, and the blood serum profile of the insulin in the mammal is monitored to provide a blood serum profile. A microporation system is then used to create openings in the skin of the mammal. Insulin is next delivered to the mammal through the openings by placing an insulin reservoir over the area of skin wherein the openings had been formed and the blood serum insulin levels are monitored and a blood serum profile is prepared. In accordance with the present inventive subject matter, the blood serum profile of the mammal with the insulin delivered via the openings mimics the blood serum profile of the mammal after the insulin is administered subcutaneously via the insulin pump. The optimization of the mean opening depth of the openings formed by the microporation system allows for this to be achieved.

Additionally, a bolus injection of insulin may be administered by subcutaneous injection to the mammal and the blood serum levels are monitored to provide a blood serum profile. A microporation system is then used to create openings in the skin of the mammal. Insulin is next delivered to the mammal through the openings by placing an insulin reservoir over the area of skin wherein the openings had been formed and adding and active flux enhancement system to force the insulin molecules through the openings into the mammal at a higher flux rate than achieved when only passive diffusion provides the delivery of the insulin. This active flux enhancement may be pressure, an electric field to provide and electromotive force on the insulin molecules moving them into the mammal or acoustic energy to accelerate the diffusion of the insulin into the mammal. Once again the blood serum insulin levels are monitored and a blood serum profile is prepared. In accordance with the present inventive subject matter, the blood serum profile of the mammal with the insulin delivered via the openings and the active flux enhancement mimics closely the blood serum insulin profile of the mammal after the insulin bolus is administered via subcutaneous injection. The optimization of the mean opening depth of the openings formed by the microporation system allows for this to be achieved.

A further aspect of the present inventive subject matter is drawn to evaluating the effectiveness of a microporation system and drug delivery using the same by determining the trans-epidermal water loss (TEWL) across a membrane. In conducting a TEWL measurement, the amount of water crossing the membrane per unit area per unit time is measured following microporation of the membrane. A TEWL measurement may be a quantitative measurement of the mean depth of the pores made in a membrane by a microporation system within the unit area being measured as a higher measurement of the water flux rate across the membrane indicates that the micropores formed by the microporation system are, on average, of a depth that allowed more fluid to cross the membrane. In the specific case of human skin, the water content of the various layers of the epidermis are reasonably well characterized and the variations in the TEWL measurements per unit area per micropore can be correlated to indpendant measurements of the micropore mean depth.

A positive relationship exists between TEWL readings and micropore mean depth wherein a high amount of water crossing the membrane, indicates deeper mean microporation, while a low TEWL reading indicates shallower mean microporation. Extending this to the previously established relationship between mean opening depth and permeant flux rates, a high TEWL reading correlates with higher flux rates of the permeant across the membrane, while a low TEWL measurement correlates with lower flux rates of the drug across the membrane. For the purposes of the present inventive subject matter, a TEWL measurement greater than 25 provides good results for the delivery of hydromorphone. Preferably, for the administration of hydromorphone, the TEWL measurement is from about 25 to about 45. A TEWL measurement greater than 50 provides good results for the administration of insulin. Preferably, the TEWL measurement is from about 50 to about 65 for the delivery of insulin.

Care must be taken when measuring the TEWL of an individual. If the patient is sweating when the TEWL measurement is taken, then a falsely high reading will result. Thus, it is important to measure the TEWL under conditions in which the patient is comfortable and not sweating. A computer controlled standardized method with specially developed algorithms to minimize the unrelated variables possible with TEWL measurements for acquiring high quality TEWL readings in the clinic has been developed.

One such TEWL measuring device provided by DermaLab and is Model #EN60601-1. Various probes are available to be used with this measuring device. In addition, the software accompanying the measuring device allows for reading of the TEWL measurements in accordance with the following protocol: 1) make sure the TEWL is in the "Stop" mode; 2) choose "SET UP" from the menu provided by the software; 3) choose "ENVIRONMENT" and record the "RH" and "TEMP"; 4) choose "EXIT"; 5)start the DasyLab 3.5 program on the computer connected to the TEWL measuring device; 6) using the mouse, click on "START"; 7) place the probe over the desired site with cover in place, skin side down; 8) click "Collect" from the available options; 9) wait for the 60 second timer to complete; 10) record the "20 sec. Mean" and "20 Sec SD". This is just one illustrative example of a TEWL measuring device and accompanying software, and is not meant to be limiting to the present inventive subject matter in any way. Other such TEWL measuring systems may also be used in conjuction with the present inventive subject matter.

While the above aspects of the present inventive subject matter discuss delivering a permeant through a membrane, the present inventive subject matter also contemplates extracting a substance from a mammal by way of delivery openings. Thus, the present inventive is also drawn to a method for extracting a substance from an animal comprising forming a plurality of delivery openings in a membrane of the animal, with a majority of the plurality of delivery openings having a mean opening depth within the range of about 40 to about 90 microns, and extracting a substance from the animal by way of the openings.

Other aspects of the various and preferred embodiments of the present inventive subject matter are found in the following examples. The following examples are illustrative of preferred embodiments of the invention and are not to be construed as limiting the invention thereto.

EXAMPLE 1

This example demonstrates a method for measuring the depth of openings created by a microporation system.

Human cadaver skin tissue was obtained through the National Disease Research Interchange (NDRI) and the Cooperative Human Tissue Network (CHTN). One tissue was provided as a 10 cm by 10 cm full thickness sample with considerable adipose tissue present (NDRI#0041785). The location of harvest was unknown. The sample was collected on 10 Nov 2000 at 8 hours post-mortem and immediately frozen post-harvest. The sample was shipped on 16 Jan 2001 and maintained at −66° C. upon receipt at Altea Therapeutics. The donor was a non-diabetic Caucasian female, aged 50 with no history of skin disease. Cause of death is reported as probable myocardial infarction.

The cadaver skin was prepared and sectioned into individual samples of approximately 2 cm by 4 cm. Each sample was thawed and sectioned for use and measurement on the same day. During method development, two sample mounting devices were used: (1) Acrylic slide with Velcro or (2) closed cell foam with staples to retain the sample.

Either sample mounting device was held in place on the 3-axis stage by clamps. The video microscope objective was held in position over the stage with rigid laboratory ring stands and spring clamps. Focus (movement in the 'Z' axis) and sample positioning (movement in the 'X' and 'Y' axis to select individual pores to measure) were controlled by manually the operator adjusting the position of the 3-axis stage. The output of the video microscope was connected to the Sony media converter. The Svideo output of the media converter was connected to the Imagex Marking and Measurement System and subsequently displayed on the 13" television monitor. The digital output of the media converter was connected to the PC and captured as individual still images using the Ulead Video Studio software. An Imagex system was designed to make a variety of measurement calculations, such as length in x and y, linear path length, or planar area, directly from a video screen. The Imagex system was calibrated in both the x and y direction using a 100 division per millimeter reticle (Pyser-SGI Ltd Graticules, UK). The reticle was placed on the 3-axis stage and oriented manually such that the scale was horizontal on the display screen. The calibration function of the Imagex system was used to calibrate the device at a length of 100 μm. The calibration was validated by making measurements of the same reticle at various lengths and orientations (vertical, horizontal, arbitrary) and positions within the field of view. The dimensional was also validated by measuring objects of known width (50 and 80 μm diameter tungsten wires).

A Sony digital indicator was used to record distance moved in the Z-direction by the stage. The spring-loaded indicator was positioned such that the end of the gauge rested on the flat surface of the stage. The zero function of the device was used to record the distance between the top surface of the skin and the bottom surface of a micropore.

Given a fixed-focus optical system with a shallow depth of field, the pore depth is equal to the distance the sample must be moved to give sharp focus on the top surface of the skin and on the bottom of the micropore. The objective used was a 100× on a Scalar video microscope with a depth of field resolution of +/−5 microns.

At the initiation of this example, the entire 10×10 cm sample of skin was thawed. Subcutaneous adipose tissue was surgically removed. The sample was subdivided and frozen. On each day of data collection, sufficient sample was thawed and sectioned for use on that day. After thawing and mounting, the surface of the skin was swabbed with alcohol to mimic the procedure as executed in vivo. An array of micropores was created in each sample using the desired experimental parameters. After creation of the pores, a small drop of green food coloring was wiped over the area with pores. After approximately 5-10 seconds the food coloring was removed by blotting gently with an absorbent tissue. This process highlights the edges of each micropore but does not stain unmicroporated tissue.

A digital still photograph was recorded using the Ulead software. The "distance" or "path length" functions of the Imagex system were used to measure both the length and width of the pore. The distance function measured only horizontally or vertically, so each sample was positioned as close as possible to align with the axis of measurement of the system. If alignment was less than optimal, the "path length" function was used to measure both length and width of a micropore. The "area" function of the Imagex system allowed the user to trace the perimeter of an area of arbitrary shape and then displayed the planar area defined by that shape. For each opening, the most obvious "top" edge of the pore was traced and the area recorded.

Within the limitation of the shallow depth of field, the operator brought the top surface of the skin adjacent to the edge of the pore being measured into sharp focus. Having determined the position of the top surface of the skin, the digital indicator is zeroed and then the stage is moved in the 'Z' direction incrementally until the bottom of the micropore is in sharp focus. The distance the stage moved between focus points is recorded as pore depth. In some instances, wherein the edge morphology of the skin about the circumference of the pore had significant variance in height, several such measurements were made on a single pore until the operator felt comfortable that a reasonable 'mean' pore depth number could be established for that pore. In addition, to ensure that the operator component of this measurement system was negligible, multiple different operators were used to measure the same sets of micropores and the results were then compared. In all such comparisons between different operators measuring the same sets of micropores, the mean depth for a set of 80 pores was found to be within 9 microns and the standard deviation of depths over the 80 pore samples where virtually identical.

FIG. 1 shows the results of pore depth measurements of pulse-limited planar pores and an early prototype system which used 80-micron tungsten wires in a step and repeat process to form the array of pores.

Figure 2:
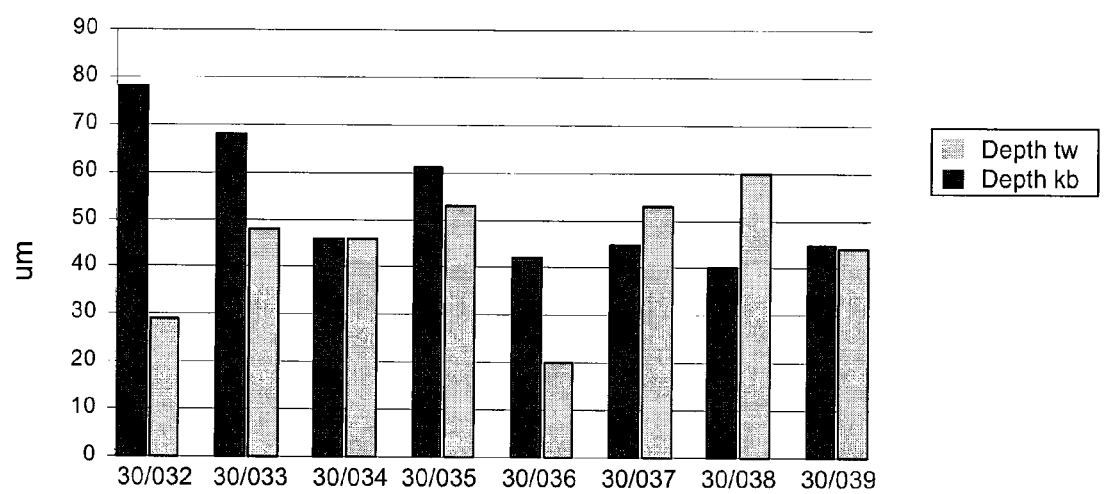
FIG. 2 depicts the depth measurement of a series of delivery openings made by two different operators.

FIG. 2 shows the inter-operator variability of depth measurements on the same 8 openings made in cadaver skin in accordance with the above procedure. Depth measurement differences ranged from 0 to 62%; however, given the limited sample size, the average depth measured by both operators was 53±14 and 44±13 microns.

EXAMPLE 2

This example demonstrates using a second generation microporation system (a "planar array" microporator) to achieve the micropore depth of an early prototype microporation system (a "step and repeat" microporator).

Figure 3:
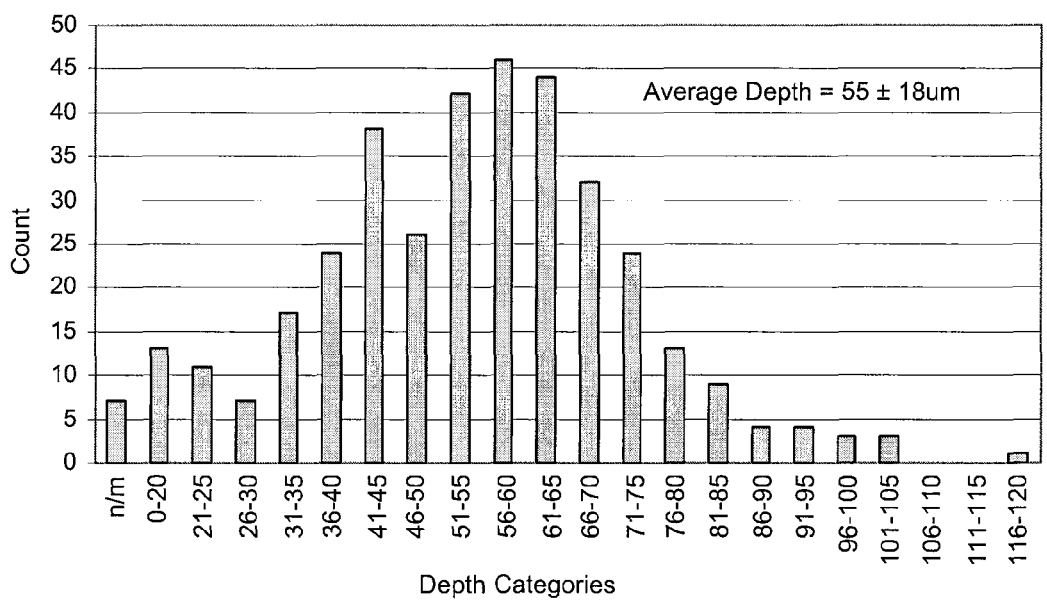
FIG. 3 represents the depth distribution for delivery openings created with the step and repeat microporation system.

An early prototype microporation system was used to generate an opening or an array of micropores in human donor skin. The depth of the micropores was measured using the method provided in Example 1. The distribution of the depths of the micropores is given in FIG. 3. The average depth was 55±18 microns. This value was used to evaluate a second generation microporation system using a planar array microporator with an activator.

Test 1

Multiple micropore patterns were created using a planar microporator array and activator and parameter settings from the clinical study (Activator model AACT-01, shielded arrays, 5 msec×4 pulse 100 opto) were examined on two skin donors.

| Micropore Depth With AACT-01 at 5 msec × 4 pulse 100 opto | | | |
|---|---|---|---|
| Pattern | No. of pores | Average Depth | Median Depth |
| Pattern 1 (Donor # 40346) | n = 80 | 44 + 8 | 44.5 |
| Pattern 2 (Donor # 40346) | n = 80 | 24 + 11 | 23 |
| Pattern 3 (Donor # 40346) | n = 80 | 26 + 9 | 26 |
| Pattern 4 (Donor # 41785) | n = 80 | 34 + 14 | 33.5 |
| Pattern 5 (Donor # 41785) | n = 52 | 35 + 13 | 35 |
| Total | n = 372 | 33 + 13 | 32 |

The observed micropore depths did not achieve the target and were considerably shallower than expected. The data implied that the poor delivery observed in the clinic was a result of shallow micropore formation and that more input energy would achieve the target and allow improved drug delivery.

Subsequent comparisons of the TEWL readings taken during these clinical trials also confirmed that the TEWL measurements indicated shallower pores than had been expected.

Test 2

It was necessary to characterize the effect of varying each device parameter on micropore depth to determine suitable input energy adjustments.

A faster rise time activator would induce a more volatile better removal of skin tissue by creating a higher peak pressure during the flash vaporization of the tissue being ablated and thus create micropores more efficiently. A faster rise time activator was built (AACT-02) and the tested concurrently with the parameter characterization.

| Effect of varying parameter combinations on average micropore depth | | | | |
|---|---|---|---|---|
| Parameter combination | No. of pores | Average Depth | Median Depth | % > 40M |
| 5 msec × 4 pulse opto 100 | n = 80 | 52 ± 19 | 54 | 78.75 |
| 2 msec × 2 pulse opto 100 | n = 80 | 20 ± 7 | 19 | 0 |
| 2 msec × 4 pulse opto 100 | n = 80 | 42 ± 19 | 43 | 42.5 |
| 2 msec × 8 pulse opto 100 | n = 80 | 31 ± 19 | 25 | 26.25 |
| 2 msec × 16 pulse opto 100 | n = 80 | 40 ± 24 | 33 | 30 |
| 2 msec × 32 pulse opto 100 | n = 80 | 41 ± 13 | 40.5 | 47.5 |
| 2 msec × 2 pulse opto 25 | n = 80 | 16 ± 7 | 17 | 0 |
| 2 msec × 2 pulse opto 50 | n = 80 | 0 | 0 | 0 |
| 2 msec × 2 pulse opto 100 | n = 80 | 20 ± 7 | 19 | 0 |
| 2 msec × 2 pulse opto 200 | n = 80 | 23 ± 10 | 22.5 | 3.75 |
| 2 msec × 2 pulse opto 400 | n = 80 | 17 ± 7 | 16 | 0 |
| 2 msec × 4 pulse opto 25 | n = 80 | 56 ± 19 | 60 | 68.75 |
| 2 msec × 4 pulse opto 50 | n = 80 | 24 ± 9 | 23 | 1.25 |

Effect of varying parameter combinations on average micropore depth

| Parameter combination | No. of pores | Average Depth | Median Depth | % > 40M |
|---|---|---|---|---|
| 2 msec × 4 pulse opto 100 | n = 80 | 42 ± 19 | 43 | 42.5 |
| 2 msec × 4 pulse opto 200 | n = 80 | 28 ± 10 | 25 | 5 |
| 2 msec × 4 pulse opto 400 | n = 80 | 42 ± 13 | 40.5 | 45 |
| 2 msec × 8 pulse opto 25 | n = 80 | 28 ± 16 | 23 | 16.25 |
| 2 msec × 8 pulse opto 50 | n = 80 | 47 ± 14 | 48 | 55 |
| 2 msec × 8 pulse opto 100 | n = 80 | 31 ± 19 | 25 | 26.25 |
| 2 msec × 8 pulse opto 200 | n = 80 | 20 ± 10 | 19 | 3.75 |
| 2 msec × 8 pulse opto 400 | n = 80 | 22 ± 13 | 20 | 8.75 |

There was not an observable trend as the number of pulses or the color temperature changed.

Upon reviewing these results, multiple hypotheses were put forth to explain the observations. These included array to array variations, differences in donor skins, differences in mounting/staining/measurement techniques, and variability in the array to skin energy transfer at each poration filament (i.e., poor contact).

Test 3

The 5 msec×4 pulse data from Test 2 suggested the faster rise time activator did improve the efficiency with which the micorpores were made. Because the data was from a single pattern, the test needed to be repeated. There was also a need to address some of the hypotheses that evolved from the data in Test 2. Multiple patterns were created on a single donor using the faster rise time activator (model AACT-02).

Micropore Depth With AACT-02 at 5 msec × 4 pulse 100 opto

| Pattern | No. of pores | Average Depth | Median Depth | % > 40 uM |
|---|---|---|---|---|
| Test 2 (Donor # 48562) | n = 80 | 52 ± 19 | 54 | 81.3 |
| Pattern 1 (Donor # 40346) | n = 80 | 40 ± 16 | 40 | 27.5 |
| Pattern 2 (Donor # 40346) | n = 80 | 26 ± 13 | 24 | 16.3 |
| Pattern 3 (Donor # 40346) | n = 80 | 20 ± 12 | 17.5 | 3.75 |
| Pattern 4 (Donor # 40346) | n = 80 | 37 ± 15 | 34.5 | 38.8 |
| Total | n = 400 | 35 ± 19 | 32 | 33.5 |

The repeated measurements did not corroborate the data from test 2. In fact, the data was very similar to the data obtained from the slower rise time activator (AACT-01) suggesting that rise time may not have an impact on micropore depth. To follow-on, the same settings were used to create 2 additional patterns on the same donor and 2 patterns on a new donor. All four patterns were created using the same array.

Micropore Depth With AACT-02 at 5 msec × 4 pulse 100 opto

| Pattern | No. of pores | Average Depth | Median Depth | % > 40 uM |
|---|---|---|---|---|
| Total from Test 3 | n = 400 | 35 ± 19 | 32 | 33.5 |
| Pattern 1 (Donor # 40346) | n = 80 | 42 ± 15 | 41 | 52.5 |
| Pattern 2 (Donor # 40346) | n = 80 | 39 ± 15 | 37 | 45 |
| Pattern 3 (Donor # 26685) | n = 80 | 37 ± 16 | 35 | 33.8 |
| Pattern 4 (Donor # 26685) | n = 80 | 38 ± 15 | 36 | 41.3 |
| Total | n = 720 | 37 ± 17 | 35 | 41.2 |

The different skin samples did not appear to affect the micropore depth. Although the cumulative measurements were very similar using the same planar array, the correlation between the patterns on a per filament basis was relatively weak.

Test 4

Based on the variability and lack of obvious trends in the data, it was concluded that there was a high probability that the energy was not consistently being transferred from each filament in an array to the skin. This may be due to flexing of the array away from the skin or the filaments of the array may be embedded in the adhesive and plastic shield. To test this hypothesis, the arrays were mounted on a firm plastic piece with a vacuum port. The plastic piece supported the fingers of array, preventing flexing away from the skin, and allowed a vacuum to be applied to the skin. The vacuum ensured positive contact between the array and skin by pulling the skin up around the filaments during activation. Two patterns were created with the fast rise time activator (AACT-02) and the 5 msec×4 pulse 100 opto parameter combination with and without vacuum.

Average micropore depth using AACT-02 at 5 msec × 4 pulse 100 opto with and without vacuum

| Condition | No. of pores | Average Depth | % > 40 uM |
|---|---|---|---|
| No Vacuum applied | n = 80 | 90 ± 28 | 92.5 |
| 25 in Hg Vacuum applied | n = 80 | 201 ± 55 | 71.3 |

The data indicates that positive contact improves energy transfer and generates significantly deeper micropores. The data also suggests that with positive contact much less input energy is required to reach the target level established earlier. The next step is to quickly screen a number a parameter combinations to narrow in on a setting that had a high potential for delivery.

Effect of pulsewidth on average micropore depths with and without vacuum Single pulse, 25 opto, 10 random micropores measured per pattern

| Condition | No. of pores | Average Depth | Median Depth |
|---|---|---|---|
| 1 msec × 1 pulse - No Vac | n = 10 | 0 | 0 |
| 1 msec × 1 pulse - 15 in Hg vac | n = 10 | 35 ± 15 | 41 |

Effect of pulsewidth on average micropore
depths with and without vacuum
Single pulse, 25 opto, 10 random micropores
measured per pattern

| Condition | No. of pores | Average Depth | Median Depth |
|---|---|---|---|
| 2 msec × 1 pulse - No Vac | n = 10 | 0 | 0 |
| 2 msec × 1 pulse - 15 in Hg vac | n = 10 | 44 ± 23 | 38.5 |
| 3 msec × 1 pulse - No Vac | n = 10 | 38 ± 8 | 37.5 |
| 3 msec × 1 pulse - 15 in Hg vac | n = 10 | 59 ± 14 | 62 |
| 4 msec × 1 pulse - No Vac | n = 10 | 33 ± 9 | 33.5 |
| 4 msec × 1 pulse - 15 in Hg vac | n = 10 | 62 ± 11 | 61.5 |
| 5 msec × 1 pulse - No Vac | n = 10 | 36 ± 14 | 33 |
| 5 msec × 1 pulse - 15 in Hg vac | n = 10 | 59 ± 17 | 60.5 |

A random group of parameter combinations was also tested to help identify potential candidates for clinical application.

Effect of various parameter combinations on average micropore depths
All used 25 opto setting

| Condition | No. of pores | Average Depth | Median Depth | % > 40 uM |
|---|---|---|---|---|
| 0 msec × 2 pulse - 15 in Hg vac | n = 80 | 31 ± 13 | 29 | 25 |
| 1 msec × 1 pulse - 15 in Hg vac | n = 80 | 46 ± 16 | 49 | 65 |
| 1 msec × 2 pulse - 15 in Hg vac | n = 80 | 54 ± 9 | 56 | 81.3 |
| 1 msec × 3 pulse - No Vac | n = 80 | 29 ± 13 | 28.5 | 8.75 |
| 1 msec × 5 pulse - No Vac | n = 80 | 66 ± 11 | 65 | 98.8 |
| 1 msec × 5 pulse - No Vac (2) | n = 80 | 66 ± 13 | 66 | 90 |
| 3 msec × 1 pulse - No Vac | n = 80 | 32 ± 14 | 33 | 21.3 |
| 3 msec × 2 pulse - No Vac | n = 80 | 52 ± 14 | 51.5 | 75 |

Test 5

Surprisingly, the 1 msec×5 pulse 25 opto setting without vacuum seems to approach the target micropore morphology. The plastic backing supporting the array fingers prevented array flex and improved contact between the array and skin. Adding a less flexible plastic backing to the current array set up was a relatively simple modification, but dramatically increases depth and improves the potential for drug delivery. The tests were repeated with multiple patterns on multiple donors.

Examination of 1 msec × 5 pulse 25 opto setting with multiple donors
Activator AACT-02 and modified array

| Donor | No. of pores | Average Depth | Median Depth | % > 40 uM |
|---|---|---|---|---|
| 26791 (n = 2 patterns, 2 arrays) | n = 160 | 66 ± 12 | 66 | 94.4 |
| 27744 (n = 2 patterns, 2 arrays) | n = 160 | 58 ± 14 | 58 | 39.4 |
| 27978 (n = 4 patterns, 2 arrays) | n = 320 | 53 ± 13 | 52 | 76.3 |
| 26882 (n = 2 patterns, 2 arrays) | n = 160 | 89 ± 24 | 90 | 94.4 |
| Total | n = 800 | 65 ± 21 | 61 | 74.5 |

Test 6

An exhaustive and robust data set testing the modified array, fast rise time activator (AACT-02), and new device parameters was generated. Human donor skin was taken from the freezer (−67° C.) into normal saline at room temperature. The samples were allowed to equilibrate for 75 minutes then blotted dry and mounted on a skin distention unit. Four patterns of micropores were created on each sample, with a new array being used each time, and stained. The activator head was applied with 3 pounds of force for all patterns. The rise time was recorded for each pulse on each of the patterns.

Examination of 1 msec × 5 pulse 25 opto setting with multiple donors
Activator AACT-02 and modified array

| Donor | No. of pores | Temp | Average Depth | Median Depth | % > 40 uM |
|---|---|---|---|---|---|
| 41802 (n = 4 patterns) | n = 320 | 20.5° C. | 46 ± 17 | 46 | 59.7 |
| 25422 (n = 4 patterns) | n = 320 | 19.3° C. | 48 ± 14 | 47 | 64.4 |
| 27813 (n = 4 patterns) | n = 320 | 20.3° C. | 65 ± 16 | 64 | 92.5 |
| 41213 (n = 4 patterns) | n = 320 | 19.1° C. | 59 ± 17 | 57 | 85.9 |
| 26765 (n = 4 patterns) | n = 320 | 21.0° C. | 56 ± 34 | 44 | 41.9 |
| 24697 (n = 4 patterns) | n = 320 | 21.1° C. | 59 ± 17 | 57 | 86.9 |
| 24692 (n = 4 patterns) | n = 320 | 20.1° C. | 73 ± 22 | 69 | 88.8 |
| 26800 (n = 4 patterns) | n = 320 | 20.6° C. | 58 ± 15 | 55 | 86.9 |
| 25830 (n = 4 patterns) | n = 320 | 21.6° C. | 70 ± 19 | 72 | 87.5 |
| 26401 (n = 4 patterns) | n = 320 | 21.9° C. | 60 ± 22 | 56 | 80 |
| Total | 3200 | | 59.4 ± 21 | 57 | 77.4 |

The average depths were consistently within the target range and the depth distribution looked very similar to the distribution achieved with the early prototypes. With all the planar array configurations tested on human donor skin, certain individual micropores were labeled non-measurable ("n/m"). With the earlier planar array configurations, the majority of n/m's were simply too shallow to measure. It seemed the filament left an impression in the skin that attracted the stain, but there was no discernible depth. In this test, though, the majority of n/m's were qualitatively different. The filament appeared to make a micropore with appreciable depth, but when the array was removed the edges of the micropore seemed to fold over on each other. Under the microscope these n/m's appeared as slits. Although the n/m's observed during this test are more likely micropores, it is unclear whether these micropores are viable for delivery. This type of 'folded over' micropores are the sort which can be measured using the fluorescent tracers and/or confocal microscope techniques described above.

EXAMPLE 3

This example demonstrates the ability to deliver a small molecular drug, hydromorphone, across a biological membrane using a microporation system.

All chemicals were purchased from Fisher Scientific except hydromorphone (Sigma). Hairless mice (strain: SHK1) were purchased from Charles River Labs (Wilmington, Mass.). A microporation system in accordance with the present inventive subject matter was provided and used to create micropores in the stratum corneum (75 micropores/$cm^2$). The skin samples were mounted in Franz Cells, which accommodate donor phase in the top chamber and receptor phase in the bottom chamber, with the skin sample mounted in between the two chambers. An HP/Agilent 1100 HPLC system was used for sample analysis.

The donor compartment contained 10 mg/ml hydromorphone hydrochloride unless otherwise specified. Both the donor and receptor compartments contained 50 mM phosphate buffer at pH 7.5. Hairless mouse skin was harvested immediately prior to the experiments. The hairless mouse skin was soaked in 50 mM phosphate buffer to remove residual enzymes and blood.

The mice in the microporation group had an array of micropores created on the mouse skin after harvesting and washing. The control group (intact skin) had no micropores. The skin was then mounted on Franz cells filled with receptor phase. The sample volume was 500 µl for all samples taken and fresh receptor solution was used to replace the sampled volume in the receptor. Samples at time zero sample were taken immediately after the donor phase was added to the donor compartment. Samples were taken every hour for 8 hours. Samples were analyzed by reversed phase HPLC using UV detection.

The cumulative amount of hydromorphone delivered was measured in samples taken from the receptor compartment. In the first experiment, delivery through microporated skin was compared to intact skin for a hydromorphone concentration of 1 mg/ml. The amount of hydromorphone delivered at 8 hours was 18 times higher for microporated skin when compared to intact skin at 1 mg/ml.

The effect of donor compartment concentration on the amount delivered was then tested by evaluating 0.1, 1.0, 5.0, 10.0 mg/ml. The amount of hydromorphone delivered through microporated skin at 8 hours for 10 mg/ml was 13 times higher when compared to the amount delivered for 1 mg/ml.

The results demonstrated that microporation is an effective approach to enable the delivery of hydromorphone through freshly excised hairless mouse skin. The hydromorphone flux through intact skin was minimal. The flux rate and amount delivered is proportional to the concentration of the hydromorphone solution in the donor compartment over an 8-hour time period.

EXAMPLE 4

This example illustrates the ability of the microporation system to mimic the delivery of a subcutaneous infusion of insulin. Hairless rats were purchased and dosed with insulin in accordance with the terms set forth below. The insulin concentration within the serum of the rats was then monitored at given time intervals to provide a blood serum insulin concentration profile.

Control

Figure 4:
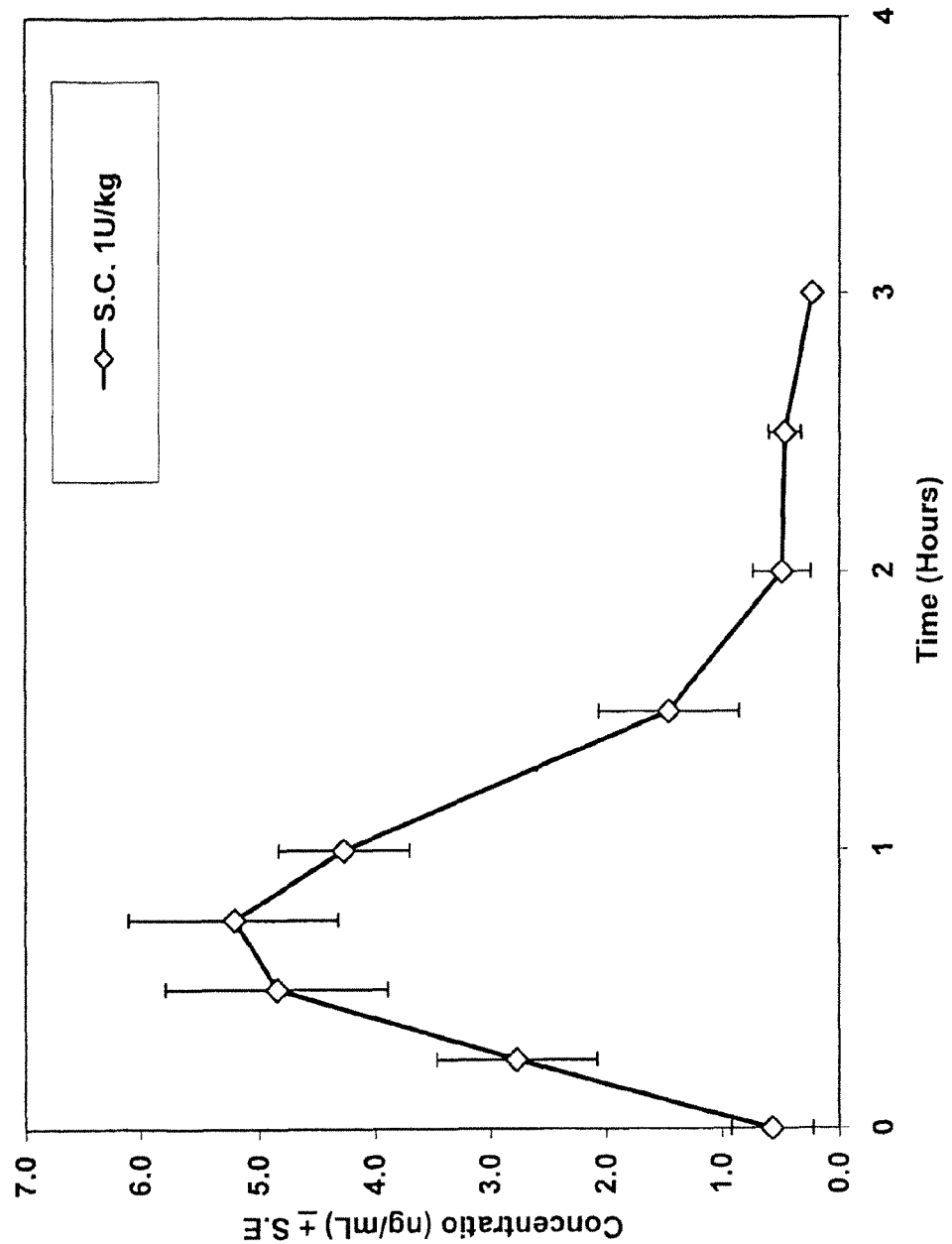
FIG. 4 is a serum insulin concentration profile for subcutaneous delivery of insulin.

Three hairless rats were given a 1 U/kg dose of insulin by way of subcutaneous administration. The concentration of insulin in the rats' blood serum was monitored. The average insulin blood serum concentration for the three rats was determined. A plot of the average insulin serum concentration (ng/ml) for the three rats versus time is provided in FIG. 4.

Test 1

Five hairless rats were purchased from Charles River. Jugular vein cannulation was performed the day before the experiment to allow the animals recovering from the surgery.

The experiment was conducted as follows. The rats were anesthetized immediately before the skin treatment, which consisted of cleaning the abdomen side of the rat skin with an alcohol swab. The abdomen was allowed to air dry.

After the abdomen dried, the microporation system was placed longitudinally, and the bottom corners marked, on the cleaned skin site. The cleaned skin site was then microporated using the microporation system. Following microporation, the microporation system was removed and a liquid reservoir patch was placed on the microporated area. The patch was then filled with a 50 IU/ml dose of insulin and a time-zero sample was immediately taken. The remaining samples were taken according to the preset schedule.

After the sample at the $4^{th}$ hour was taken, the rats were anesthetized to retrieve the donor solution from the liquid reservoir patch. Blood sampling continued until the $8^{th}$ hour.

Figure 5:
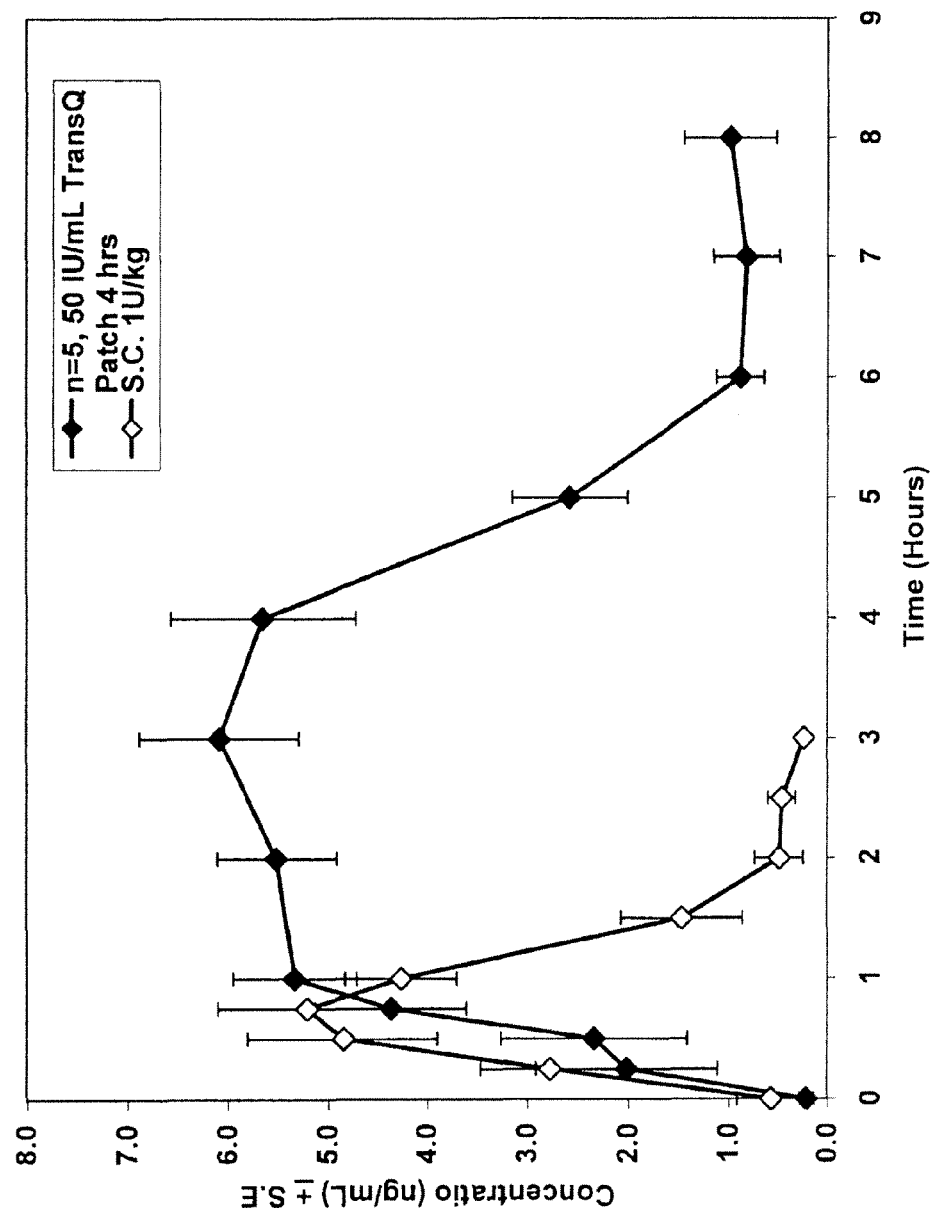
FIG. 5 is a serum insulin concentration profile for transdermal delivery of a 50 IU/ml dose of insulin following microporation of the membrane.

The average concentration of the five rats was determined and an insulin serum concentration profile was developed. FIG. 5 is a chart showing the average insulin serum concentration (ng/ml) versus time for the control rats above and the rats in this test. As can be seen in the figure, the rats to which the insulin was delivered transdermally through micropores exhibited a higher average concentration of insulin in their serum. The rats of test 1 also had a longer duration of a higher average insulin serum concentration. The patch was applied to the rats for four hours, and the profile indicates a high concentration of insulin for those four hours, with the concentration decreasing only after the patch was removed.

Thus, this test shows that the transdermal administration of insulin to rats results in a higher average insulin serum concentration for a longer period of time when compared with the rats to which the insulin was administered subcutaneously.

Test 2

Four hairless rats were purchased from Charles River. Jugular vein cannulation was performed the day before the experiment to allow the animals recovering from the surgery.

The experiment was conducted as follows. The rats were anesthetized immediately before the skin treatment, which consisted of cleaning the abdomen side of each rat skin with an alcohol swab. The abdomen was allowed to air dry.

After the abdomen dried, the microporation system was placed longitudinally, and the bottom corners marked, on the cleaned skin site. The cleaned skin site was then microporated using the microporation system. Following microporation, the microporation system was removed and a liquid reservoir patch was placed on the microporated area. The patch was then filled with a 50 IU/ml dose of insulin and a time-zero sample was immediately taken. The remaining samples were taken according to the preset schedule.

After the sample at the $4^{th}$ hour was taken, the rats were anesthetized to retrieve the donor solution from the liquid reservoir patch. Blood sampling continued until the $8^{th}$ hour.

In the first part of this test, the patch applied to the rats' microporated abdomens had an area of 1 cm². Afterward, the test was conducted again, however the patch applied was 2 cm² in area. Lastly, the test was performed for a third time, with the patch having a size of 3 cm².

Figure 6:
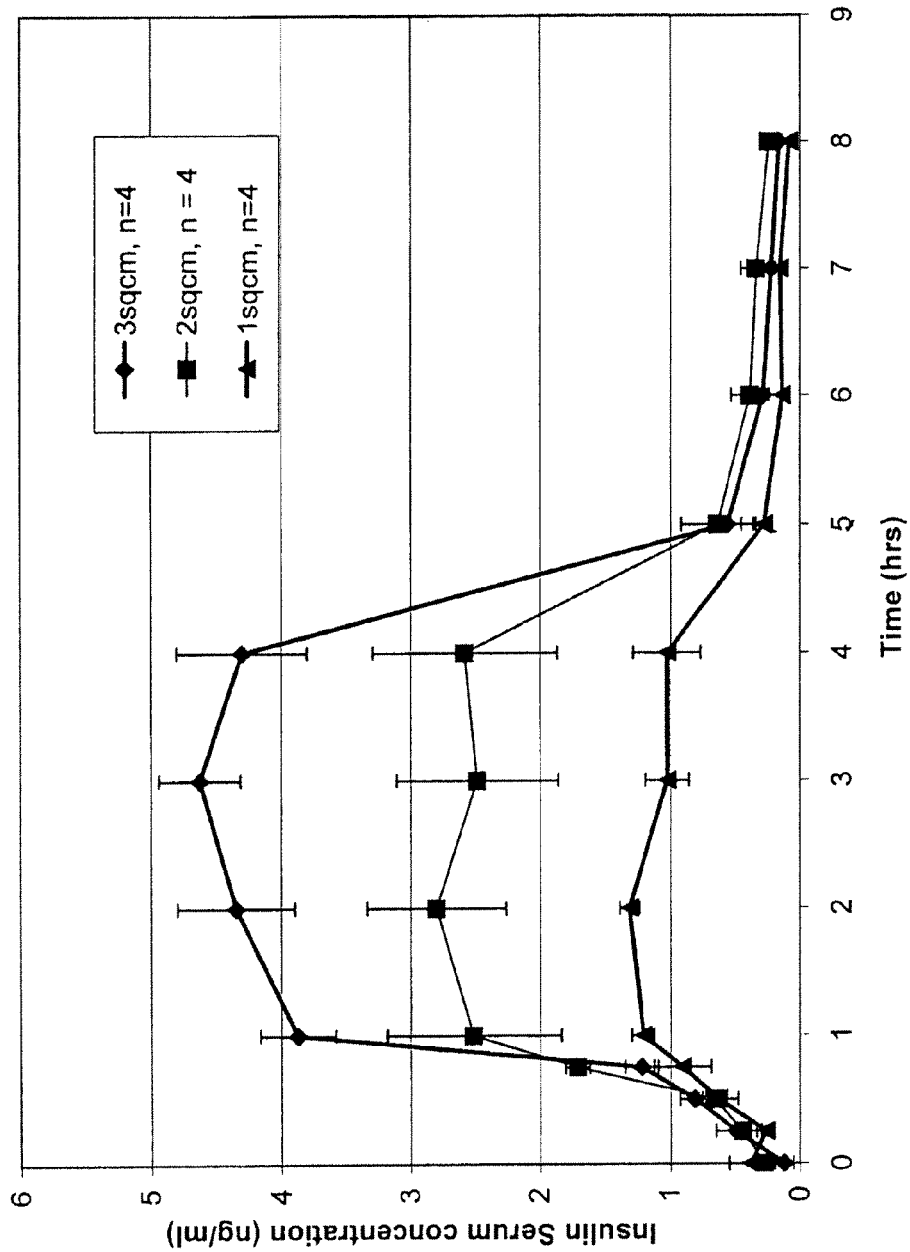
FIG. 6 is a serum insulin concentration profile for transdermal delivery of a 50 IU/ml doses of using various sizes for the transdermal patch.

The average concentration of the four rats was determined for each patch size and an insulin serum concentration profile was developed. FIG. 6 is a chart showing the average insulin serum concentration versus time for the rats with the different patch sizes.

As can be seen by FIG. 6, the average insulin serum concentration roughly doubled when the patch size was increased from 1 cm² to 2 cm². Further, the average insulin concentration also roughly doubled when the patch size was increased from 2 cm² to 3 cm².

Test 3

Three hairless rats were prepared and tested in accordance with the procedure set forth in Test 1 above. However, for this test, a second generation planar microporation system was used to create the micropores in the abdomen of each rat. In addition, the transdermal patch contained a 50 IU/ml dose of insulin when applied to the microporated area of the skin of each rat.

The insulin serum concentration was monitored in each of the rats at various intervals of time. The average concentration of the three rats was determined and an insulin serum concentration profile was developed.

Figure 7:
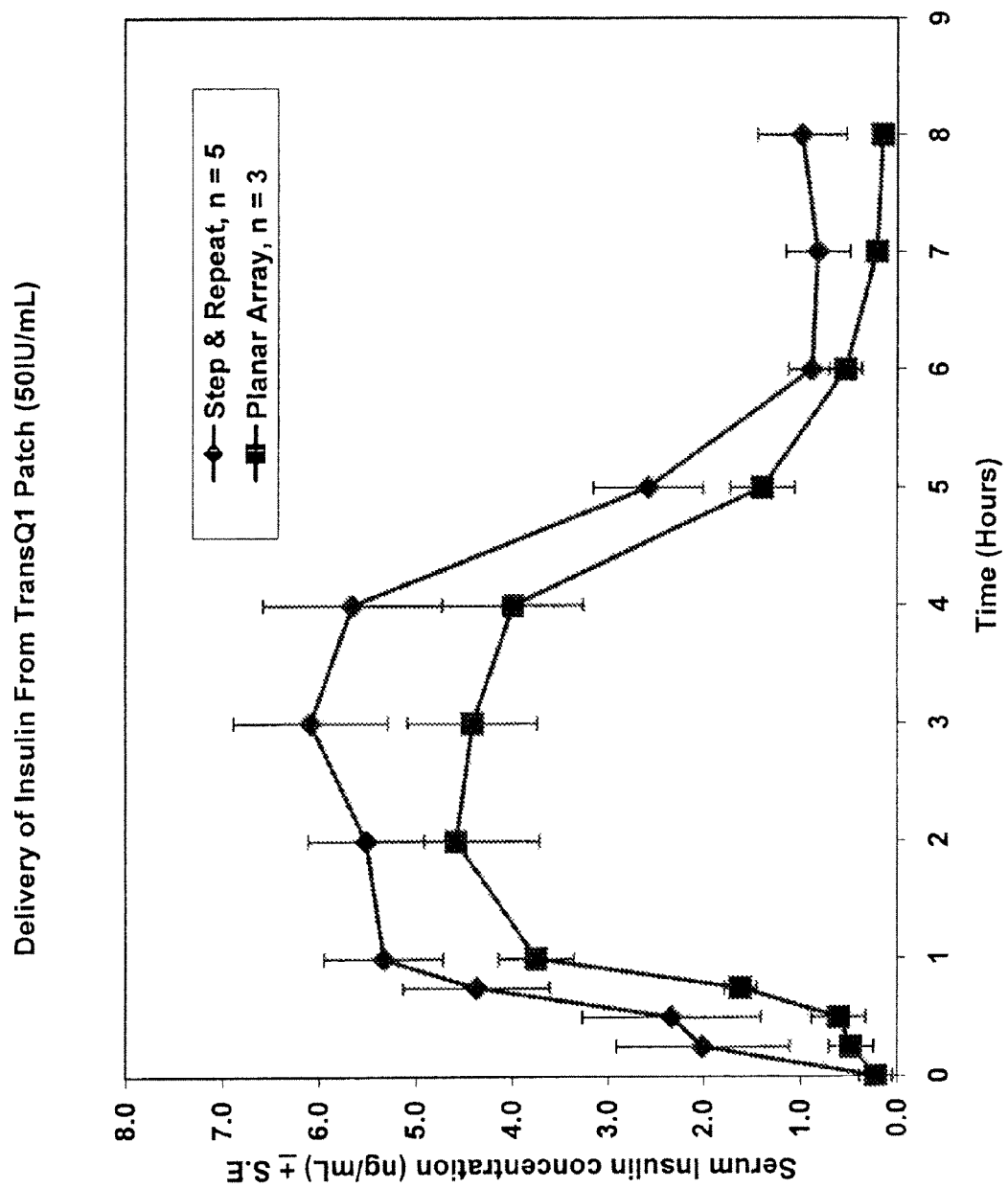
FIG. 7 is a serum insulin concentration profile for transdermal delivery of a 50 IU/ml dose of insulin following microporation using an early prototype microporation system and a second generation microporation system.

FIG. 7 is a chart showing the average insulin serum concentration versus time for the rats in Test 1 and the rats in this test. As can be seen in the figure, the rats to which the insulin was delivered transdermally through micropores in Test 1 exhibited a higher average concentration of insulin in their serum than the rats of this test. The patch was applied to the rats for four hours in each test, and the profile indicates a high concentration of insulin for those four hours, with the concentration decreasing only after the patch was removed.

It is interesting to note that, while the insulin serum concentration for the rats in this test (planar array microporation system) is slightly lower than the concentration for the rats in Test 1 (step and repeat microporation system), the shape of the profiles is consistent. This may be due to the depth of the micropores formed by the step and repeat microporation system being greater than the depths of the micropores formed by the planar array microporation system.

Test 4

This test was designed to determine any differences in the types of transdermal patches used to deliver insulin through the micropores. Five hairless rats were prepared and tested in accordance with the procedure set forth in Test 1 above. Following microporation of each rat, an early prototype liquid reservoir patch was applied to two of the rats, while a second generation transdermal patch was used to deliver insulin in the remaining three rats. Each patch contained a 50 IU/ml dose of insulin when applied to the microporated area of the skin of each rat.

The insulin serum concentration was monitored in each of the rats at various intervals of time. The average concentration of the three rats was determined and an insulin serum concentration profile was developed.

Figure 8:
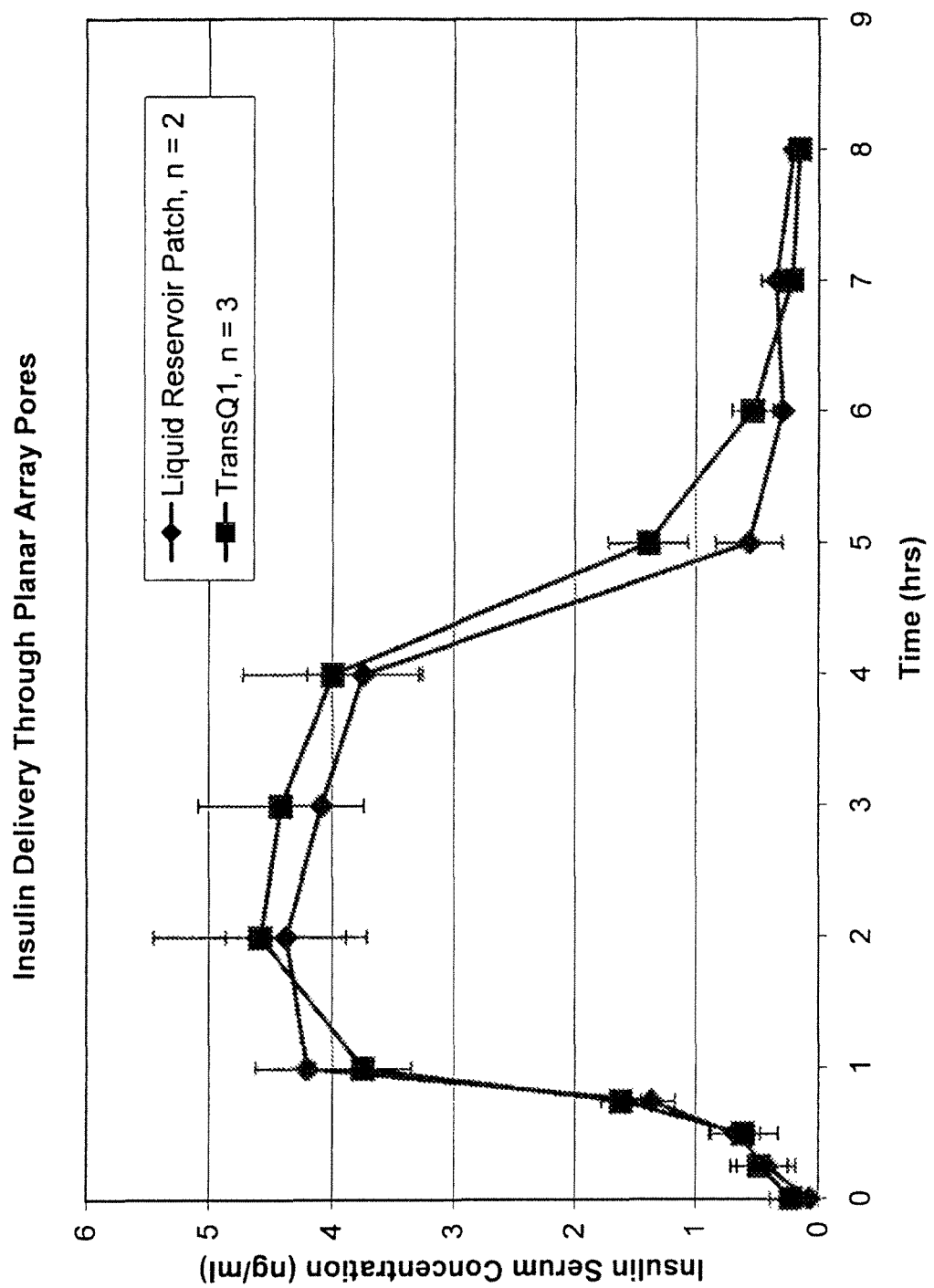
FIG. 8 is a serum insulin concentration profile for delivery of insulin using different transdermal patches.

FIG. 8 is a chart showing the average insulin serum concentration versus time for the rats broken out by the generation of patch used. As can be seen by the data, the average insulin concentration was very similar for the two types of patches.

Test 5

This test was set up to determine the effect of dose concentration on the serum insulin profile for hairless rats.

A number of rats were prepared in accordance with the procedure set forth in Test 1 above. For those rats that had delivery openings formed on their abdomen, the delivery openings were formed using an early prototype microporation system. Insulin was delivered to the rats using a second generation delivery patch containing the desired concentration of insulin.

In this test, three rats did not receive delivery openings. The delivery patch was applied to the rats' abdomen without microporation. The rats in this control group were given a 50 IU/ml concentration dose of insulin.

For the other rats in this test, the delivery patch contained insulin in concentrations of 10 IU/ml (6 rats), 25 IU/ml (6 rats), IU/ml (5 rats) or 100 IU/ml (6 rats). The insulin serum concentration was monitored in each of the rats at various intervals of time. The average concentration of the rats for that particular insulin concentration (and whether delivery openings were formed or not) was determined and an insulin serum concentration profile was developed.

Figure 9:
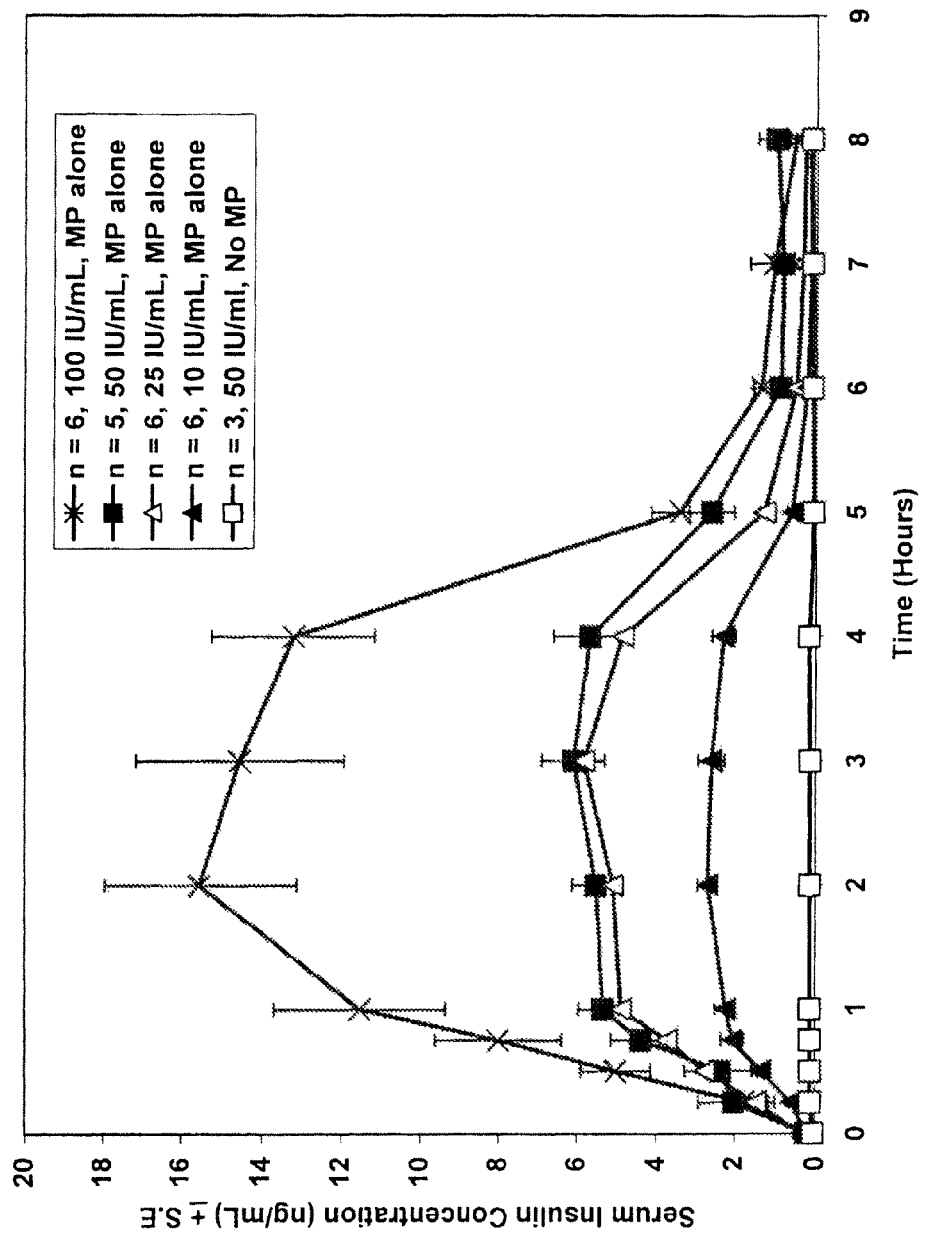
FIG. 9 is a serum insulin concentration profile for delivery of insulin using different dose concentrations.

FIG. 9 is a chart showing the average insulin serum concentration versus time for the rats broken out by the insulin concentration used in the dose supplied to the rats. As can be seen by the data, the average insulin concentration was very low for those rats that did not have delivery openings formed. Also, the average insulin serum concentration for the rats to which a 100 IU/ml dose of insulin was administered was very high in comparison to the rats receiving other doses. Interestingly, not much difference is seen between the rats receiving the 50 IU/ml dose and the rats receiving the 25 IU/ml dose.

EXAMPLE 4

This example demonstrates the correlation between a trans-epidermal water loss (TEWL) measurement and the effective delivery of hydromorphone.

A series of human volunteers, recruited under and IND filed with the FDA and the appropriate IRB for the specific protocol being conducted had a patch of skin prepared for microporation. Following microporation of the skin, the TEWL measurement was taken and hydromorphone was delivered to the mammal via a transdermal patch. The steady state serum concentration between 1 and 4 hours (Css(1-4 hrs)) value was determined for the hydromorphone, and the TEWL measurement taken for the microporated skin. The TEWL measurements were taken with a standard TEWL measuring device (provided by Cyberderm).

The results are shown in the table below:

| Patient No. | Css (1-4 hrs) Measurement | TEWL Measurement |
|---|---|---|
| 1015 | 1100 | 44.1 |
| 1016 | 1200 | 32.2 |
| 1022 | 1300 | 29.3 |
| 1023 | 300 | 20.4 |
| 1026 | 700 | 43.8 |
| 1027 | 350 | 19.3 |
| 1029 | 700 | 33.5 |
| 1030 | 400 | 29.5 |
| 1031 | 100 | 9.2 |
| 1032 | 225 | 22 |
| 1033 | 200 | 20.1 |
| 1015 | 600 | 32.4 |
| 1018 | 300 | 15.4 |
| 1027 | 350 | 16.5 |
| 1032 | 125 | 13.1 |
| 1033 | 100 | 15.7 |

A higher Css reading generally correlates with a more effective dose of drug, or at least the patient feeling that the drug is working better. In this example, the higher Css values correlated with the higher TEWL measurement. Care was taken to make certain that the subject was comfortable and that the room temperature was a constant 70-72° F., meaning that the microporated area of skin was not sweaty.

The inventive subject matter being thus described, it will be obvious that the same may be varied in many ways. Such variations are not to be regarded as a departure from the spirit and scope of the inventive subject matter, and all such modifications are intended to be included within the scope of the following claims.

What is claimed is:

1. A method for delivering permeant substances through a biological membrane of an animal comprising forming a plurality of delivery openings in the membrane, wherein an opening depth of the majority of said delivery openings falls within the range between 40 and 90 microns, and delivering a permeant through the plurality of delivery openings by placing a patch comprising the permeant over the plurality of delivery openings,
    wherein the plurality of delivery openings are formed by microporation conducted with positive pressure being present between a microporator and said membrane, wherein said positive pressure results from a vacuum of about 0.25 to about 0.80 bar being applied between said microporator and said membrane.

2. The method of claim 1 wherein the opening depth of a majority of said delivery openings falls within the range of 50 to 70 microns.

3. The method of claim 2 wherein 75% of said delivery openings have an opening depth falling within the range of 50 to 70 microns.

4. The method of claim 3 wherein 75% of said delivery openings have an opening depth falling within the range of 55 microns to 65 microns.

5. The method of claim 1 wherein said delivery openings have a range of opening depths falling within one standard deviation of 50 microns to 70 microns.

6. The method of claim 5 wherein said delivery openings have a range of opening depths falling within one standard deviation of 60 microns.

7. The method of claim 1 wherein said delivery openings have a range of opening depths falling within one standard deviation of 90 microns.

8. The method of claim 1 wherein the plurality of delivery openings are formed by a planar array microporation device.

9. The method of claim 1 wherein the plurality of delivery openings are formed by a microporator selected from the group consisting of a heated probe element capable of conductively delivering thermal energy via direct contact to a biological membrane to cause the ablation of some portion of the membrane deep enough to form a micropore, the heated probe comprising an electrically heated resistive element capable of ablating a biological membrane or an optically heated topical dye/absorber layer, electro-mechanical actuator, a microlancet, an array of microneedles (solid or hollow), microprojections, microcstructures or lancets, a sonic energy ablator, a laser ablation system, and a high pressure fluid jet puncturer.

10. A method for delivering drugs transdermally into a biological membrane of an animal comprising forming a plurality of delivery openings through a membrane, wherein said delivery openings have a distribution resulting in a bell-shaped curve with said delivery openings having a mean opening depth of between 40 and 90 microns, and delivering a drug through the plurality of delivery openings by placing a patch comprising the drug over the plurality of delivery openings,
    wherein the plurality of delivery openings are formed by microporation conducted with positive pressure being present between a microporator and said membrane, wherein said positive pressure results from a vacuum of about 0.25 to about 0.80 bar being applied between said microporator and said membrane.

11. The method of claim 1 wherein said positive pressure results from a vacuum of about 0.50 bar being applied between said device and said membrane.

12. The method of claim 10 wherein said positive pressure results from a vacuum of about 0.50 bar being applied between said device and said membrane.

* * * * *